US012667391B2

(12) United States Patent
Larosa et al.

(10) Patent No.: US 12,667,391 B2
(45) Date of Patent: Jun. 30, 2026

(54) MODULAR BONE FASTENER ASSEMBLIES WITH BIASED ANGLE RECEIVERS

(71) Applicant: Orthofix US LLC, Lewisville, TX (US)

(72) Inventors: Frank Larosa, Lewisville, TX (US); Emily Rafalko, Lewisville, TX (US); Allyson Versluys, Denton, TX (US)

(73) Assignee: Orthofix US LLC, Lewisville, TX (US)

( * ) Notice: Subject to any disclaimer, the term of this patent is extended or adjusted under 35 U.S.C. 154(b) by 0 days.

(21) Appl. No.: 18/734,098

(22) Filed: Jun. 5, 2024

(65) Prior Publication Data

US 2024/0423679 A1 Dec. 26, 2024

Related U.S. Application Data

(60) Provisional application No. 63/509,091, filed on Jun. 20, 2023.

(51) Int. Cl.
*A61B 17/70* (2006.01)
*A61B 17/86* (2006.01)
(52) U.S. Cl.
CPC ...... *A61B 17/7032* (2013.01); *A61B 17/7035* (2013.01); *A61B 17/8685* (2013.01); *A61B 17/7001* (2013.01); *A61B 17/7002* (2013.01); *A61B 17/7034* (2013.01); *A61B 17/7037* (2013.01); *A61B 17/7043* (2013.01); *A61B 17/7056* (2013.01)
(58) Field of Classification Search
CPC ............ A61B 17/7032; A61B 17/7035; A61B 17/8685; A61B 17/7037; A61B 17/863;

A61B 17/70; A61B 17/7001; A61B 17/7034; A61B 17/7038; A61B 17/7041; A61B 17/7043; A61B 17/7046
USPC ....... 606/246, 250, 264, 265, 266, 267–279, 606/86 A, 914, 916
See application file for complete search history.

(56) References Cited

U.S. PATENT DOCUMENTS

| | | | |
|---|---|---|---|
| 6,280,442 | B1 | 8/2001 | Barker |
| 6,974,460 | B2 | 12/2005 | Carbone |
| 8,556,938 | B2 | 10/2013 | Jackson |
| 9,277,942 | B2 | 3/2016 | Biedermann |
| 9,554,829 | B2 | 1/2017 | Cahill |
| 10,034,691 | B1 | 7/2018 | Lish |
| 10,064,659 | B2 | 9/2018 | Biedermann |
| 10,603,082 | B2 | 3/2020 | Lish |
| 10,722,272 | B2 | 7/2020 | Biedermann |

(Continued)

*Primary Examiner* — Marcela I. Shirsat
(74) *Attorney, Agent, or Firm* — Haynes and Boone, LLP

(57) ABSTRACT

Devices, systems, and methods relating to biased angle receivers for modular pedicle screw assemblies are described herein. The receiver may include a body and a retainer. The body may be configured to be coupled to a bone fastener and a rod for spinal stabilization. The body may also include a base defining an opening from a top end to a bottom end of the base and having a bottom axis at the bottom end of the base. The bottom axis may be obliquely angled with respect to the longitudinal axis of the body. A chamber may be defined within the base and be in communication with the opening. A retainer may be disposed in the chamber and may be configured to expand in an upper section of the chamber to receive a bulbous head of the bone fastener up through a bottom opening of the retainer.

20 Claims, 14 Drawing Sheets

(56) References Cited

U.S. PATENT DOCUMENTS

| | | | |
|---|---|---|---|
| 11,154,334 B2 | 10/2021 | Biedermann | |
| 2003/0055426 A1 * | 3/2003 | Carbone | A61B 17/7037 |
| | | | 606/305 |
| 2005/0154393 A1 * | 7/2005 | Doherty | A61B 17/7038 |
| | | | 606/267 |
| 2012/0136395 A1 * | 5/2012 | Biedermann | A61B 17/7035 |
| | | | 606/279 |
| 2012/0303063 A1 * | 11/2012 | Cahill | A61B 17/7041 |
| | | | 606/267 |
| 2014/0031880 A1 * | 1/2014 | Biedermann | A61B 17/8605 |
| | | | 606/305 |
| 2019/0150990 A1 * | 5/2019 | Jackson | A61B 17/7037 |
| 2023/0200858 A1 * | 6/2023 | Park | A61B 17/7038 |
| | | | 606/265 |
| 2023/0363797 A1 * | 11/2023 | Rezach | A61B 17/7032 |
| 2024/0325055 A1 * | 10/2024 | LaRosa | A61B 17/7032 |

* cited by examiner

250

251

252

256

253

254

255

270

271

272

275

273

274

MODULAR BONE FASTENER ASSEMBLIES WITH BIASED ANGLE RECEIVERS

CROSS-REFERENCE TO RELATED APPLICATIONS

The present applications claims the benefit of, and priority to, U.S. Provisional Patent Application No. 63/509,091, filed Jun. 20, 2023, the entirety of which is incorporated by reference herein.

TECHNICAL FIELD

This disclosure is generally directed to biased angle bone fastener assemblies for implantation in an anatomy of a patient. For instance, one or more implantable assemblies may include a receiver body coupled to a bone screw and a connecting rod to retain one or more vertebrae in a desired relationship.

BACKGROUND

Various systems for connecting fasteners (e.g., pedicle screws) to elongated supports (e.g., fixation rods) for the purposes of vertebral fixation have been proposed. Although described with reference to vertebral or spinal fixation, it should be appreciated that the systems described herein may be similarly applicable to other bone structures as well.

Generally, fixation systems include a receiver (or "receiver body" or "head") which is attachable to both a fastener and a fixation rod to retain the rod in fixed relation to the fastener, and in turn, a vertebra into which the fastener is secured. Traditional receiver assemblies include a receiver and a fastener for attachment of fixation rod to a vertebra. A physician may use multiple receiver assemblies and/or multiple rods to secure the vertebrae in a desired spatial relationship. In some installations, a first rod may extend along a first side of a patient's spine and engage a first plurality of fastener assemblies each implanted in a different vertebra, and a second rod may extend along a second side of the patient's spine and engage a second plurality of fastener assemblies. In some cases, the physician may need to align the receivers so that the rod can be properly inserted. However, based on the patient's particular physiology, different receiver and/or fasteners may be needed at different locations so that the receivers can be properly aligned.

In some instances, a receiver assembly may come preassembled such that the receiver and fastener are preselected and attached to one another by the manufacturer. The assembly of the fastener and the receiver may involve special tools and trained technicians such that assembly by the physician, nurse, or surgical technician is impractical. Accordingly, the surgeon or technician may select one of these receiver and fastener assemblies based on the patient's anatomy and/or indications. Thus, the surgeon may be limited based on the variety of selections available at the time of surgery. Therefore, it may be more desirable for a medical practitioner to assemble the receiver and fastener in the operating room so that the surgeon has a wider variety of options to choose from to implant into the patient's specific anatomy. Accordingly, improved receiver profiles may be needed in particular situations so that the system can be properly oriented and aligned.

SUMMARY

The present disclosure describes implantable devices and assemblies, including a biased angle receiver that allows a rod to be inserted into the pedicle screw assembly such that it is offset from a screw. For example, a bottom of the receiver may be angled relative to the top of the receiver such that the screw can be inserted into the receiver at an angle. Further, the implantable devices of the present disclosure may allow for modular assembly before or during a spinal fixation procedure. For example, the implantable device may allow for bottom-side loading of the screw into the receiver so that various screws having various characteristics (e.g., length, diameter, etc.) can be coupled to the receiver body.

Some embodiments of the present disclosure include an implantable receiver. The implantable receiver may include a body and a retainer. The body may be configured to be coupled to a bone fastener and a rod for spinal stabilization and may have a longitudinal axis. The body may also include a base defining an opening from a top end to a bottom end of the base and having a bottom axis at the bottom end of the base. The bottom axis, which may be referred to as a chamber axis, may be obliquely angled with respect to the longitudinal axis. A chamber may be defined within the base and be in communication with the opening. The chamber may include an upper section, a lower section, and a tapered shoulder between the upper section and the lower section. A chamber axis through the chamber may be obliquely angled with respect to the longitudinal axis. The body may also include a channel oriented along the longitudinal axis and configured to receive a set screw for locking the rod to the body, where a diameter of the channel is smaller than a diameter of the upper section of the chamber. The implantable receiver may also include a retainer having a first portion and a second portion. The retainer may be disposed in the chamber between the upper section and the lower section. The retainer may be configured to expand in the upper section of the chamber to receive a bulbous head of the bone fastener up through a bottom opening of the retainer. The first portion of the retainer may be wider than the lower section of the chamber.

In some embodiments, the upper section of the chamber may be wider than the lower section. In some embodiments, the first portion of the retainer is wider than the second portion. In some embodiments, a top axis of the base may be co-linear with the longitudinal axis. In some embodiments, the chamber axis and the bottom axis may be co-linear. In some embodiments, a top of the upper section of the retainer may be proximate the top end of the base and a bottom of the lower section of the retainer may be proximate the bottom end of the base. In some embodiments, the body may have two opposing arms extending upwardly from the top end of the base and defining two lateral openings for receiving the rod through the channel. In some embodiments, the base may further include a lip disposed at a bottom of the lower section of the chamber and extending around at least a portion of a circumference of the lower section of the chamber. In some embodiments, an outer surface of the body may include a conical taper surrounding the chamber, the conical taper being oriented obliquely to the longitudinal axis.

Some embodiments of the present disclosure include an implantable receiver. The receiver may include a body, a retainer, and a pressure cap. The body may be configured to be coupled to a bone fastener and a rod for spinal stabilization, and may have a longitudinal axis. The body may also include a base defining an opening from a top end to a bottom end of the base and having a bottom axis of the bottom end of the base. The bottom axis may be obliquely angled with respect to the longitudinal axis. A chamber may be defined within the base and be in communication with the opening. The chamber may include an upper section, a lower section, and a tapered shoulder between the upper section and the lower section. A chamber axis through the chamber may be obliquely angled with respect to the longitudinal axis. The retainer may be disposed in the chamber between the upper section and lower section. The retainer may be configured to expand in the upper section of the chamber to receive a bulbous head of the bone fastener up through a bottom opening of the retainer. A pressure insert may be disposed in the opening at the top end of the base. The pressure insert may include a downward-facing surface configured to contact a head of a bone fastener. The pressure insert may be configured to apply a downward force on the head of the bone fastener when a rod is secured in the receiver.

In some embodiments, the body may further include a channel oriented along the longitudinal axis and configured to receive a set screw for locking the rod to the body. A diameter of the channel may be smaller than a diameter of the upper section of the chamber. In some embodiments, the downward-facing surface of the pressure insert may be concave. In some embodiments, the pressure insert may further include a pair of opposed sidewalls and an upward-facing surface curving between the pair of opposed sidewalls. The upward-facing surface may be saddle-shaped. In some embodiments, the opening of the body may be wider than the pressure insert such that the pressure insert is pivotable relative to the longitudinal axis. In some embodiments, the implantable receiver may further include a pin disposed in a pin hole in the body such that the pin extends into a slot in the pressure insert. The pressure insert may be pivotable about the pin relative to the longitudinal axis.

Some embodiments of the present disclosure include a modular bone fastener assembly. The modular bone fastener assembly may include a bone fastener, a receiver, and a set screw. The bone fastener may include a head comprising a spherical outer surface, a shaft extending downwardly from the head, and a neck disposed between the head and the shaft. The receiver may include a body, a retainer, and a pressure insert. The body may be configured to be coupled to the bone fastener and a rod for spinal stabilization, and may have a longitudinal axis. The body may also include a base defining an opening from a top end to a bottom end of the base, and having a bottom axis of the bottom end of the base. The bottom axis may be obliquely angled with respect to the longitudinal axis. A chamber may be defined within the base and be in communication with the opening. The chamber may include an upper section, a lower section, and a tapered shoulder between the upper section and the lower section. A chamber axis of the chamber may be obliquely angled with respect to the longitudinal axis. The body may also include a channel that may be oriented along the longitudinal axis. A diameter of the channel may be smaller than a diameter of the upper section of the chamber. The retainer may be expandable around the head and disposed in the channel between the upper and lower sections. The pressure insert may be disposed in the opening at the top end of the base. The pressure insert may include a downward-facing surface configured to contact a part of the spherical outer surface of the head. The set screw may be receivable within the channel. The set screw may be configured to apply a downward force on the rod to secure the rod within the channel and a downward force on the pressure insert and the head of the bone fastener to secure the head of the bone fastener within the receiver.

In some embodiments, the retainer may be disposed around the neck of the bone fastener. In some embodiments, the set screw may be configured to secure the head of the bone fastener between the pressure insert and the retainer. In some embodiments, the bone fastener may be pivotable relative to the bottom axis.

These and other objects, features and advantages of this invention will become apparent from the following detailed description of the various aspects and principles of the invention taken in conjunction with the accompanying drawings.

BRIEF DESCRIPTION OF THE DRAWINGS

The accompanying drawings, which are incorporated in and constitute a part of the specification, illustrate embodiments of the invention and, together with the detailed description herein, serve to explain the principles of the invention. The drawings are only for purposes of illustrating examples and are not to be construed as limiting the invention. It is emphasized that, in accordance with the standard practice in the industry, various features are not drawn to scale. In fact, the dimensions of the various features may be arbitrarily increased or reduced for clarity of discussion.

DETAILED DESCRIPTION

Figure 1:
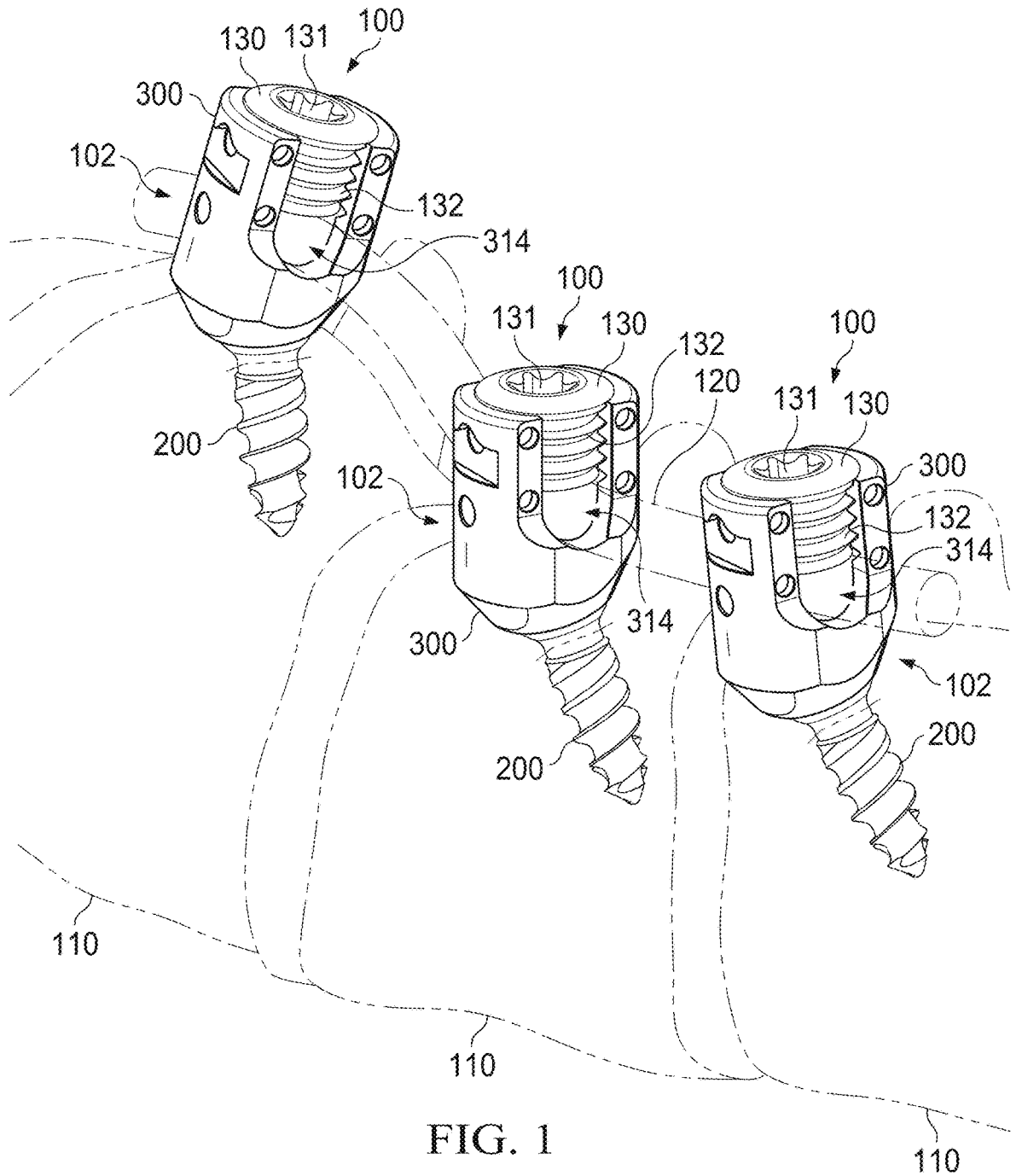
FIG. 1 is a perspective view of a spinal fixation system including biased angle pedicle screw assemblies and a connecting rod in accordance with some embodiments of the present disclosure.

For the purpose of promoting an understanding of the principles of the present disclosure, reference will now be made to the implementations illustrated in the drawings and specific language will be used to describe them. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In addition, this disclosure describes some elements or features in detail with respect to one or more implementations or figures, when those same elements or features appear in subsequent figures, without such a high level of detail. It is fully contemplated that the features, components, and/or steps described with respect to one or more implementations or figures may be combined with the features, components, and/or steps described with respect to other implementations or figures of the present disclosure. For simplicity, in some instances the same or similar reference numbers are used throughout the drawings to refer to the same or like parts.

FIG. 1 is a perspective view of a plurality of pedicle screw assemblies 100 including a plurality of implantable receivers 102 coupled to respective vertebrae 110 of a patient's spine by a plurality of screws 200. Each implantable receiver 102 in FIG. 1 includes a body 300, and may further include a retainer ring (400, FIG. 2) and a pressure cap (500, FIG. 2) as described in more detail below. The receivers 102 are coupled to one another by a rod 120 positioned in U-shaped slots or channels 314 of the receivers 102. The rod 120 may be sized, shaped (e.g., bent, curved), and otherwise structurally configured to correct a spinal deformity, and/or to retain the vertebrae 110 in a fixed position.

The positions and orientations of the receivers 102 relative to the rod 120 and the bone screws 200 may be fixed or otherwise retained by the set screws 130. For example, the bone screws 200 may be coupled to the receivers 102 in a multi-axial relationship such that the bone screws 200 may be rotated about at least one axis relative to the respective receiver 102. For example, in some aspects, one or more of the bone screws 200 may include spherical, semi-spherical, or otherwise round screw heads (not shown) seated within the receiver 102. The receivers 102 may be configured to rotate, tilt, swivel, twist, and/or otherwise move relative to the screw heads of the bone screws 200.

The receivers 102 may be biased angle receivers in which the lower part of the receiver 102 is angled with respect to a longitudinal axis of the receiver 102. The angled lower part allows the bone screws 200 to enter the bottom of the receiver 102 from an angle. In some aspects, the angled lower part also allows bone screws 200 to enter the bottom of the receiver 102 vertically up-and-down. The biased angle receivers provide for greater angulation on at least one side of the receiver 102, thus giving physicians more flexibility when installing the pedicle screw assembly 100 and placing the rod 120 and set screws 130. In some aspects, the biased angle receivers may be beneficial for applications in which a physician expects the biased angle receiver to be tilted or angled relative to the bone screw axis. For instance, as shown in FIG. 1, the bone screws 200 are driven into the vertebrae 110 along a side and at an angle relative to the sagittal plane of the spine. The receivers 102 are all tilted inward toward the sagittal plane. Thus, the biased angle receivers may be suitable for these and similar applications where some amount of angulation in a given direction can be expected. Accordingly, the physician may be more confident that the range of motion/rotation of the receivers 102 relative to the bone screws 200 will allow the physician to align the receivers 102 along a given path or axis to receive the rod 120.

With the bone screws 200 fixed to the vertebrae 110, a physician may move the receivers 102 into the orientation shown in FIG. 1 to receive the rod 120. In some embodiments, the orientations of the receivers 102 relative to one another may be maintained by the friction-fit coupling to the bone screws 200 as the physician guides the rod 120 through the channel 314. For example, the receivers 102 may include a coil or other compressible member that applies a frictional force to the head 210 to resist movement of the screw 200. In some cases, the retainer ring 400 and/or the pressure cap 500 may provide a frictional force to the screw head 210.

With the rod 120 in the channel 314, and with the desired overhang of the rod 120 from the outermost receivers 102, the set screws 130 can be tightened down to compress rod 120 and the screw heads of the screws 200 against the base of the receivers 102 to fix the position and orientation of the receivers 102 relative to the rod 120 and bone screws 200. The set screws 130 may be any suitable shape. For example, the set screws 130 may include a drive feature 131 that receives an instrument for tightening the set screw 130 to compress the rod 120 and the screw heads of the screws 200. The drive feature 131 may be hexalobe shaped as shown in the illustrated embodiment, or may be any other suitable shape including hexagonal, square, or triangular. Additionally, the set screws 130 may have threading 132 along part or all of the length. The threading 132 of the set screw 130 may threadably engage the receivers 102.

Figure 2:
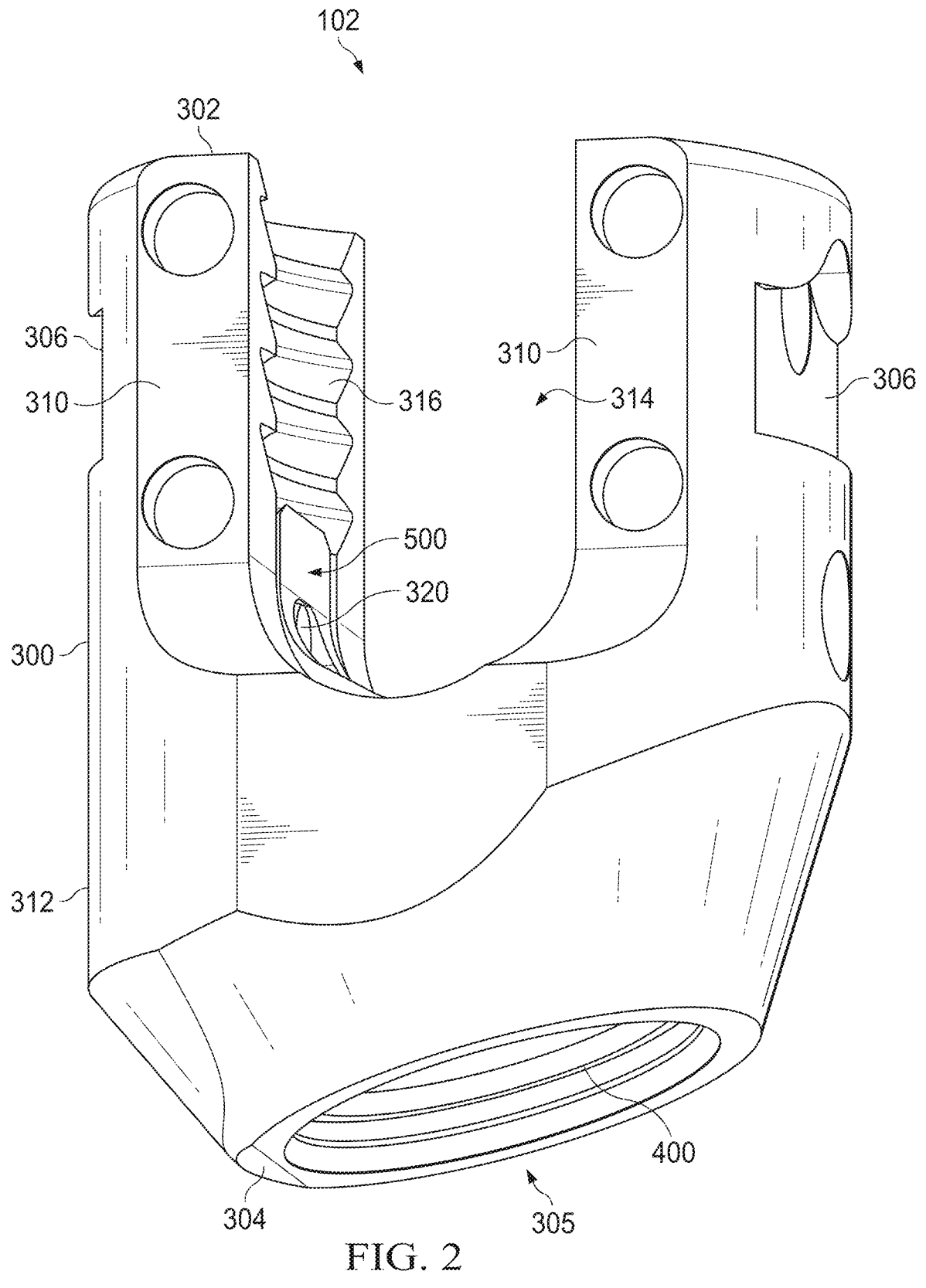
FIG. 2 is a perspective view of a biased angle receiver for a pedicle screw assembly in accordance with some embodiments of the present disclosure.

FIG. 2 is a perspective view of a receiver 102 according to an embodiment of the present disclosure. The embodiment of the receiver 102 shown in FIG. 2 may be similar or identical to the receivers 102 shown in FIG. 1. The receiver 102 includes a body 300, a retainer ring 400 or lock ring, and a pressure cap 500. The body 300 has a top end 302 for receiving a set screw (e.g., 130, FIG. 1) and a rod (e.g., 120, FIG. 1) and a bottom end 304 for receiving a screw head 210. The body 300 may further comprise an opening 305. The opening 305 may pass from the top end 302 to the bottom end 304.

The receiver 102 is a biased angle receiver where the top of the receiver 102 is aligned with a longitudinal axis and the bottom of the receiver 102 is angled with respect to the longitudinal axis. The opening 305 may follow the shape of the body 300 and be aligned with the longitudinal axis around the top then and be angled with respect to the longitudinal axis at the bottom.

In the illustrated embodiment, the body 300 is tulip-shaped, meaning the body 300 has two arms 310 on either side of the body 300 that extend from a base 312 of the body 300 to the top 302. The arms 310 define a U-shaped slot or channel 314 for seating a rod and may be referred to as sidewalls, wings, or any other suitable term. The body 300 is configured to receive a connecting rod via the channel 314. Moreover, the body 300 further includes internal threads 316 on the interior surfaces of the arms 310. The threads 316 may be configured to engage corresponding threads on a set screw (e.g., 130, FIG. 1). The set screw may be tightened down towards the base 312 to compress the connecting rod 120 onto the pressure cap 500. Compressing the pressure cap 500 may also cause the pressure cap 500 to put additional pressure onto the screw head 210 of the screw 200 to fix the receiver 102 in a desired position and orientation.

The body 300 also has two engagement features 306 that may provide for releasable engagement with a tool for inserting, positioning, and/or removing the receiver 102. For example, the engagement features 306 may provide for releasable engagement with a tool for inserting the subassembly including the receiver 102 and the connected screw 200 and driving the screw 200 into the patient's bone (e.g., vertebra). In the illustrated embodiment, the engagement feature 306 is centered with the arm 310. It will be understood that the other arm 310 may also include an engagement feature similar or identical to the engagement feature 306. The engagement feature 306 on the other arm 310 may also be centered on the arm 310. The centering of the engagement feature 306 may be beneficial for robust engagement with the insertion tool. For example, the centered placement of the engagement feature 306 may allow for a deeper groove or impression of the engagement feature 306 into the arm 310. Additional engagement features (e.g., recesses) may be provided on the flat side surfaces of the arms 310 on either side of the channel 314 to provide for better tool engagement. In another aspect, the top end 302 of the body 300 may be associated with a frangible portion or breaking line of the body 300. For example, in some embodiments, the body 300 may be integrally formed with extension or tower portions extending proximally from the top end 302 of each arm 310. The area of the body 300 comprising the top end 302 may comprise a weakened portion.

Figure 3:
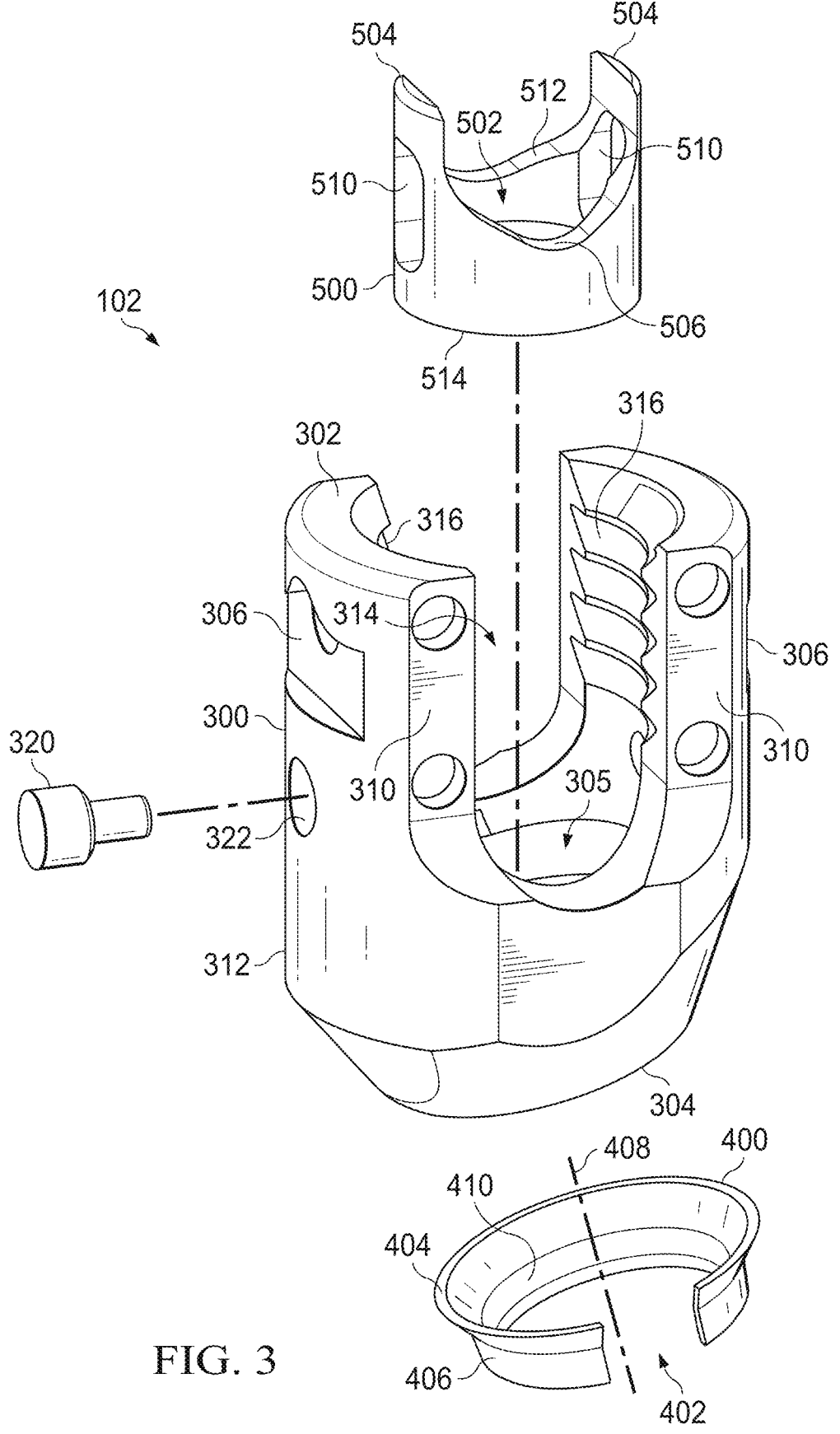
FIG. 3 is an exploded view of the receiver in FIG. 2 in accordance with some embodiments of the present disclosure.

FIG. 3 is an exploded view of the receiver 102 shown in FIG. 2 according to some embodiments of the present disclosure. The receiver 102 includes a pressure cap 500, which may also be referred to as a pressure member, pressure insert, or any other suitable term. The pressure cap 500 includes a concave upper surface or top surface 512 for receiving the connecting rod, as described above. The pressure cap 500 may be saddle-shaped, meaning it has two ends 504 with an arched surface forming a depression 506 between the two ends 504. This saddle-shape may generally match the shape of the channel 314 formed between the arms 310 of the body 300. Thus, the pressure cap 500 may be shaped to accept a rod that is placed within the channel 314 of the body 300. The pressure cap 500 may also include a concave lower surface or bottom surface 514 to contact and engage a top surface of a screw head 210. In other embodiments, the pressure cap 500 may have any suitable shape having a top surface 512 for seating a rod and a bottom surface 514 for contacting a screw head 210. For example, the top surface 512 of the pressure cap 500 may include a v-shaped depression, a rectangular depression, an elliptical depression, a hexagonal depression, and/or any other suitable shape for receiving the connecting rod. Similarly, the bottom surface 514 of the pressure cap 500 may be flat, conical, inclined, saddle-shaped and may be shaped spherically, elliptically, parabolically (e.g., paraboloid) rectangularly, hexagonally or any other suitable shape for contacting and engaging a top surface of a screw head.

Moreover, the pressure cap 500 has an opening 502 extending through the center and aligning with the opening 305 of the body 300. The opening 502 may allow an instrument to access the screw head 210 when it is inserted into the receiver 102. For example, an interfacing portion or bit of a screwdriver may be able to pass through the opening 502 of the pressure cap 500 so that the bone screw 200 may be screwed into bone.

The pressure cap 500 may be coupled to the receiver 102 via a pin 320. The pressure cap 500 has a slot 510 that is shaped to receive the pin 320. The pin 320 may be received in a pin hole 322 in the side of the body 300 such that the pin 320 projects into the opening 305 of the body 300 and through the slot 510 of the pressure cap 500. In some cases, there may be two pin holes 322 in the body 300 with a first pin hole 322 on the left side and a second pin hole 322 opposite the first on the right side. In some embodiments, there may also be a second pin 320 in the second pin hole 322 that engages a second slot 510 of the pressure cap 500. In other embodiments, a single pin 320 is used as shown in FIG. 3. A single pin configuration may allow the pressure cap 500 a greater degree of movement to tilt in response to a screw head being inserted through the bottom of the receiver 102.

The pressure cap 500 is moveable relative to the pin 320. The pressure cap 500 can move up or down the opening 305 of the body 300. The pin 320 limits the movement of the pressure cap 500. As the pressure cap 500 moves, the pin 320 moves up and down the slot 510 such that the pin 320 prevents further upward movement when it contacts the top of the slot 510 and prevents further downward movement when it contacts the bottom of the slot 510. The pin 320 may also prevent rotation of the pressure cap 500. This allows the pressure cap 500 to move up and down without uncoupling from the body 300 and while maintaining a relatively constant orientation.

In some embodiments, the width of the chamber 330 and/or opening 305 of the body 300 may be larger than a width of the pressure cap 500. Thus, the pressure cap 500 may be able to pivot within the body 300 about the pin 320. The pin 320 may continue to contact the slot 510 and prevent the pressure cap 500 from rotating relative to the body 300. The pin 320 may be welded, adhered, soldered, peened, rivetted, threadably attached, and/or otherwise affixed, attached, or coupled to the body 300. In other embodiments, the pin 320 may be formed in the body 300.

A retainer ring 400 may be included in the receiver 102. The retainer ring 400 may be a split ring that has a discontinuous annular shape configured to expand and/or retract to enlarge and/or reduce an inner diameter of the retainer ring 400 so that it is capable of expanding over a screw head 210. In other embodiments, the retainer ring 400 may be a continuous ring that is expandable over a screw head 210. The retainer ring 400 may be configured to lock the screw 200 into the receiver 102 once the screw head 210 has been inserted through a bottom opening of the retainer ring 400, as described in more detail below. Although retainer ring 400 in the form of a split ring is shown in the FIG. 3, the receiver 102 may include any suitable component that locks the screw head 210 into the receiver 102, such as spring-loaded ball bearings, yielding locking ridge, and/or any other suitable feature.

In some cases, the retainer ring 400 may include an upper surface that is configured to contact and match the shape of a lower or downward-facing surface of the screw head 210. For example, the upper surface may be spherical, rounded, tapered, or otherwise configured to cause the retainer ring 400 to expand as the screw head 210 is pressed against the retainer ring 400 to allow the screw head 210 to pass through the retainer ring 400. Once the screw head 210 has passed through the retainer ring 400, the retainer ring 400 may relax and contract around the neck of the screw 200 to lock against a lower curved surface of the screw head 210.

The retainer ring 400 may comprise an upper portion 404 and a lower portion 406. The upper portion 404 may be wider than the lower portion 406. The lower portion 406 may be arranged so that it is relatively aligned with a retainer ring axis 408 passing through the center of the retainer ring 400. The upper portion 404 may be angled away from the lower portion 406 around part or all of the circumference such that the upper portion 404 is obliquely angled relative to the retainer ring axis 408. In some embodiments, there may be an intermediate portion 410 between the upper 404 and lower 406 portions. In some cases, the intermediate portion 410 may be tapered between the upper 404 and lower 406 portions.

In other embodiments, the lower portion 406 may be angled towards or away from the retainer ring axis 408 such that both the lower portion 406 and the upper portion 404 are angled with respect to the retainer ring axis 408. In yet other embodiments, both the upper portion 404 and the lower portion 406 may be aligned with the retainer ring axis 408. In these cases, the intermediate portion 410 may have a flat or tapered ledge or ridge. In some embodiments, the intermediate portion 410 may be configured to engage the bottom surface of the screw head 210. The intermediate portion 410 may comprise a conical shape, such that the intermediate portion 410 and the screw head 210 form a circular line or ring of contact when the retainer ring 400 is retaining the screw head 210 in the body 300 (e.g., as in the position shown in FIG. 5D). In some aspects, if the screw head 210 comprises a spherical outer shape, the same circular line or ring of contact may be maintained as the screw head 210 rotates or tilts relative to the retainer ring 400. Similarly, the same ring of contact may be maintained between the screw head 210 and the bottom portion 514 of the pressure cap 500. In this way, the frictional forces that retain the orientation of the screw head 210 relative to the body 300 may be consistent for a variety of screw angles.

In some cases, the retainer ring 400 may have a different shape than that described above. For example, the retainer ring 400 may not have distinct upper 404, lower 406, and intermediate 410 portions. In some cases, the retainer ring 400 may have more portions than those described. In other cases, there may be no gap 402 in the retainer ring 400 or there may be more than one gap 402.

Figure 4A:
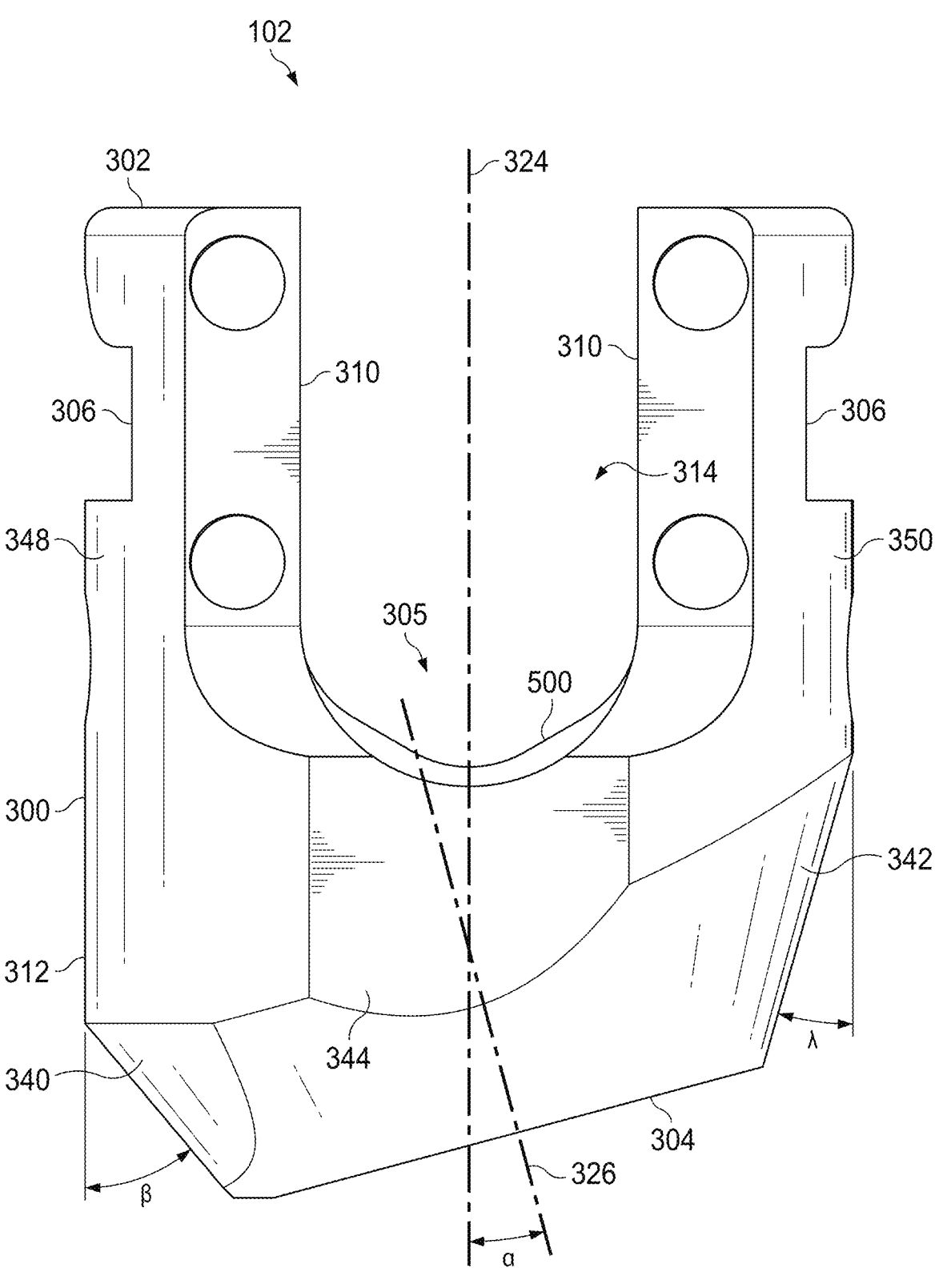
FIG. 4A is a front view of the receiver in FIG. 2 in accordance with some embodiments of the present disclosure.
Figure 4B:
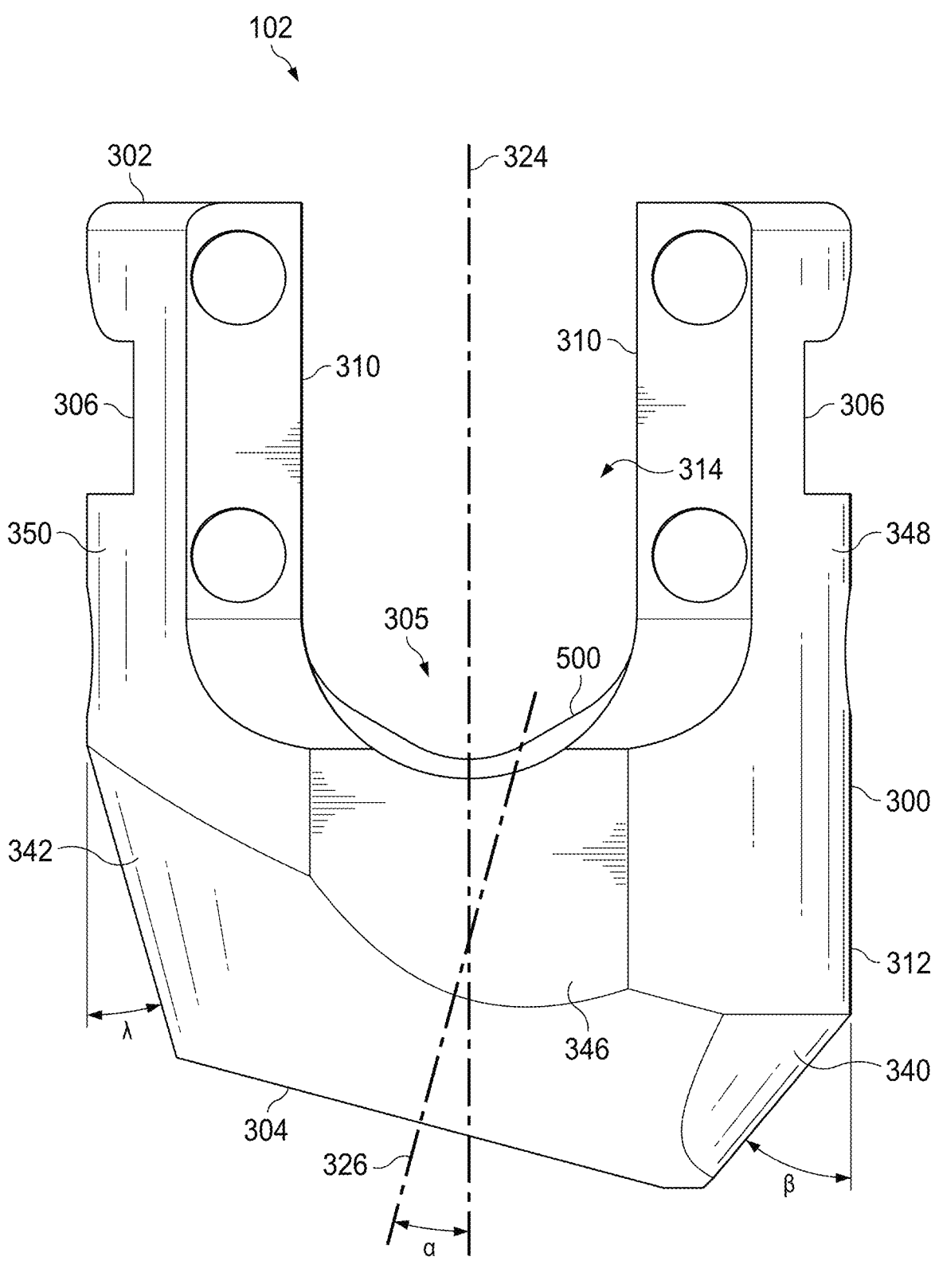
FIG. 4B is a back view of the receiver in FIG. 2 in accordance with some embodiments of the present disclosure.
Figure 4C:
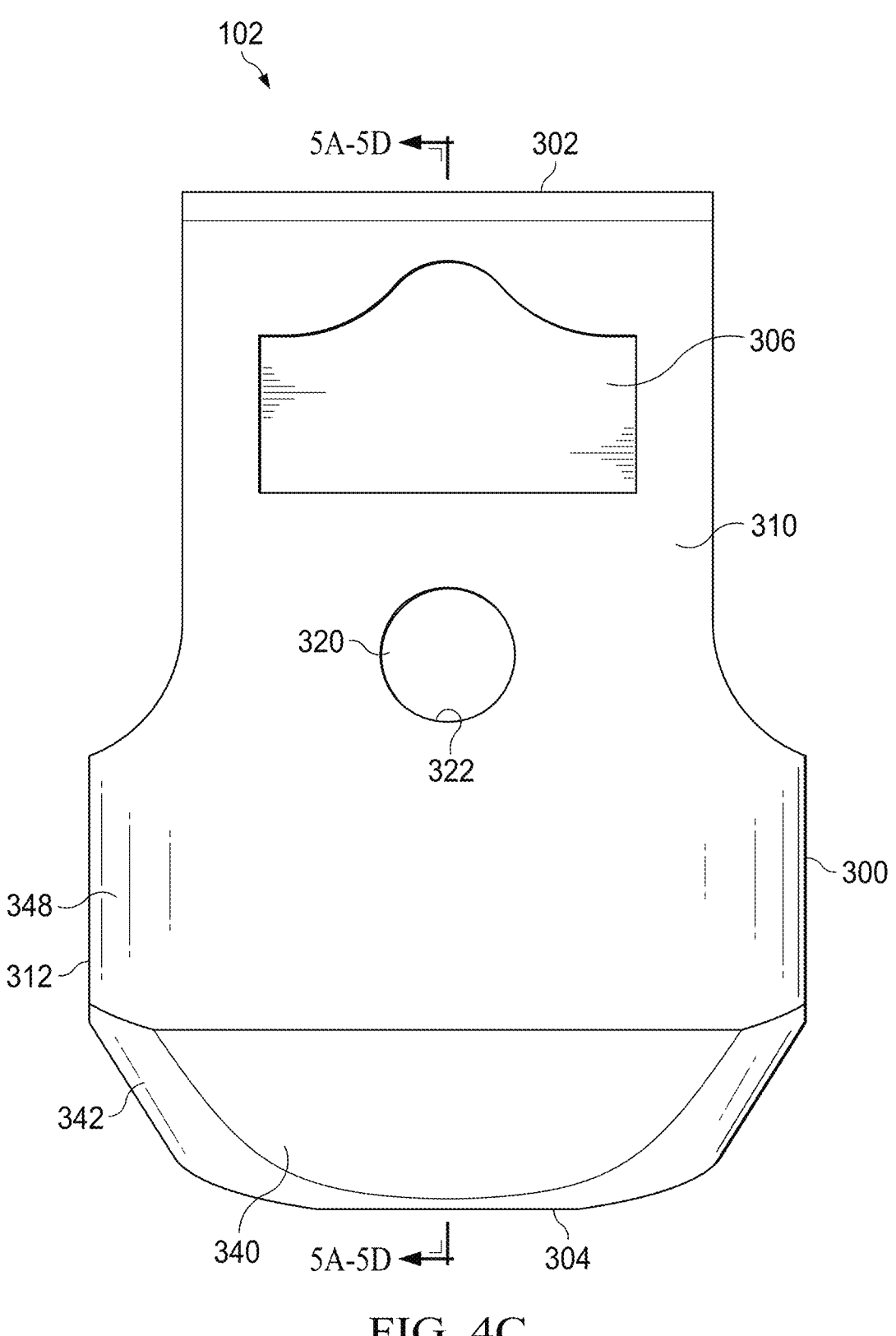
FIG. 4C is a left side view of the receiver in FIG. 2 in accordance with some embodiments of the present disclosure.
Figure 4D:
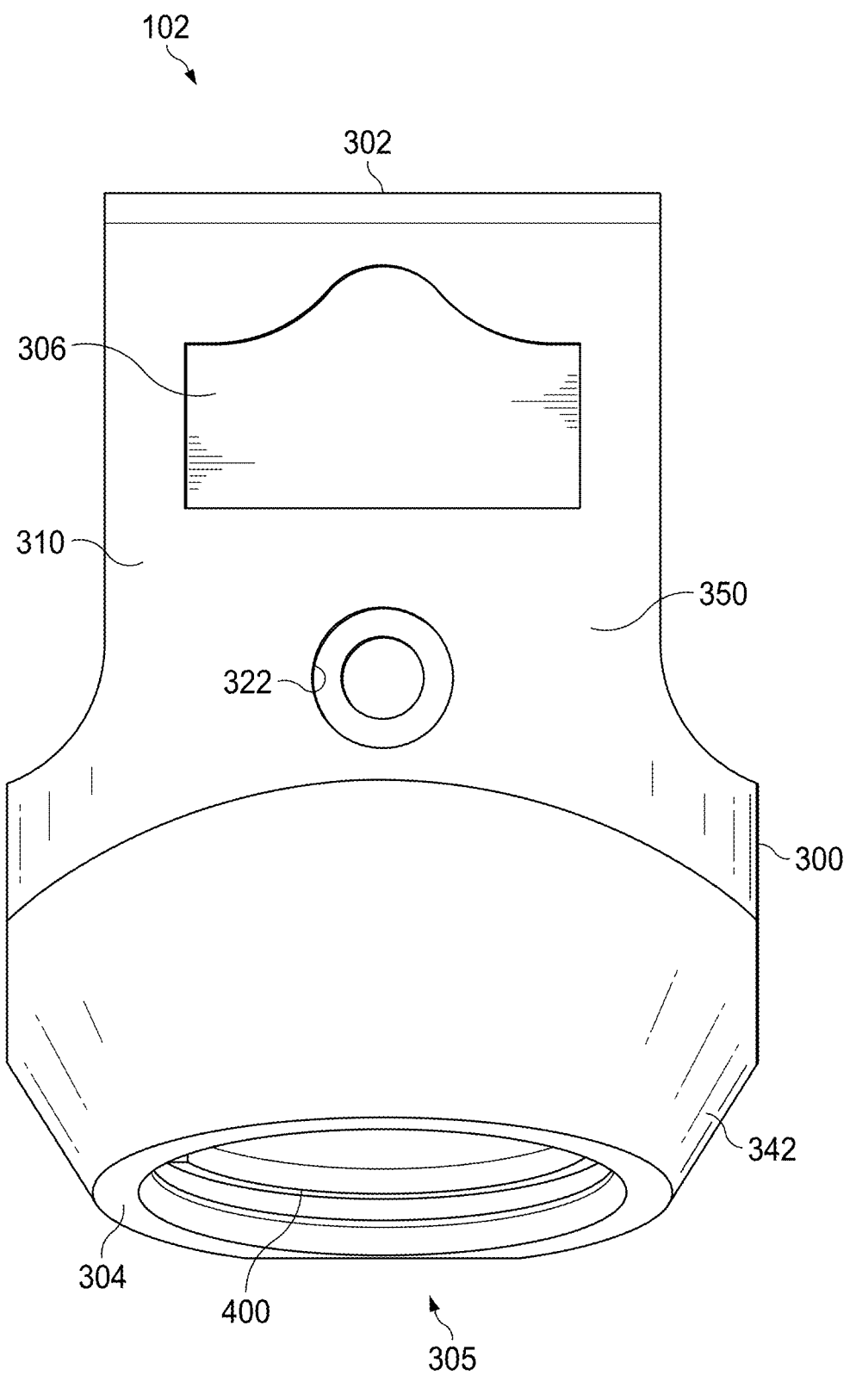
FIG. 4D is a right side view of the receiver in FIG. 2 in accordance with some embodiments of the present disclosure.

FIGS. 4A-4D show the biased angle receiver 102 shown in FIGS. 2-3 above from a variety of views according to some embodiments of the present disclosure. FIG. 4A is a front view, FIG. 4B is a back view, FIG. 4C is a left side view, and FIG. 4D is a right side view, according to some embodiments. The body 300 may have a longitudinal axis 324. The channel 314 of the body 300 may be aligned with the longitudinal axis 324 such that a rod seated in the channel 314 extends perpendicularly relative to the longitudinal axis 324. The base 312 of the body 300 angles away from the longitudinal axis 324 from the channel 314 to the bottom 304 of the body 300. A bottom axis 326 of the bottom 304 of the body 300 is obliquely angled relative to the longitudinal axis at an angle α. Thus, the opening 305 of the body 300 may change from being aligned with the longitudinal axis 324 at the top of the base 312 to being aligned with the bottom axis 326 at the bottom 304 of the body 300, as described in more detail below in reference to FIG. 5A. Angle α may be any suitable angle. For example, angle α may be any angle in a range of 0 degrees to 90 degrees.

The base 312 may have one or more tapered surfaces that define the angled portion of the base 312. In some cases, there may be a left tapered surface 340 at least partially disposed on the left side of the body 300. The left tapered surface 340 may extend part or all of the way between the top of the base 312 and the bottom 304 of the body 300. For example, as in the illustrated embodiment, the left tapered surface 340 extends between a middle portion of the base 312 and bottom portion of the base 312 proximate the bottom 304. The left tapered surface 340 may also extend at least partially around the circumference of the body 300. The left tapered surface 340 may be any suitable shape. For example, the left tapered surface 340 may include a conical taper or a flat taper and may be have any suitable shape including a polygon.

The body 300 may also have a right tapered surface 342 at least partially disposed on the right side of the body 300. The right tapered surface 342 may extend part or all of the way between the top of the base 312 and the bottom 304 of the body 300. For example, as in the illustrated embodiment, the right tapered surface 342 may extend from the top of the base 312 to the bottom 304 of the body 300. The right tapered surface 342 may also extend at least partially around the circumference of the body 300. In some cases, the right tapered surface 342 may extend around the entire circumference such that the right tapered surface 342 curves over the right side of the body 300, around the front and back of the body and under or above the left tapered surface 340. In other embodiments, the right tapered surface 342 may only curve around the right side of the body 300. In yet other embodiments, the right tapered surface 342 may curve along part or all of the front or back of the body 300 without extending to the left side or may only curve around a part of the left side. The right tapered surface 342 may be disposed generally opposite from the left tapered surface 340. The right tapered surface 342 may be any suitable shape. For example, the right tapered surface 342 may include a conical taper or a flat taper and may be have any suitable shape including a polygon.

In some cases, the left tapered surface 340 and the right tapered surface 342 may contact each other. In other cases, the left tapered surface 340 and the right tapered surface 342 do not contact each other. In some aspects, the left tapered surface 340 and the right tapered surface 342 may be defined by or otherwise associated with a single conical surface or similar three-dimensional surface. The conical surface may comprise a circular cone, an oblique cone, parabaloid, and/or any other suitable type of conical surface or similar surface. The profile of the tapered surfaces 340, 342 may beneficially reduce the amount of contact the receiver 102 has with bone and other adjacent tissues such that the receiver 102 may be oriented at the desired angle without being stopped or hindered by adjacent bone tissue.

The left tapered surface 340 may be angled from the top to the bottom. For example, the left tapered surface 340 may be angled at an angle β from the longitudinal axis 324. In some cases, the left tapered surface 340 may be oriented along the bottom axis 326 such that angle β is equal to angle α relative to the longitudinal axis 324. In other cases, the left tapered surface 340 may not be oriented along the bottom axis 326 and, thus, angle β may be different angle from angle α. For example, angle β may be in the range of 0 degrees to 90 degrees from the longitudinal axis 324.

Similarly, the right tapered surface 342 may be angled from the top to the bottom. For example, the right tapered surface 342 may be angled at an angle λ from the longitudinal axis 324. In some cases, the right tapered surface 342 may be oriented along the bottom axis 326 such that angle λ is equal to angle α relative to the longitudinal axis 324. In other cases, the right tapered surface 342 may not be oriented along the bottom axis 326 and, thus, angle λ may be different from angle than angle α. For example, angle λ may be in the range of 0 degrees to 90 degrees from the longitudinal axis 324.

The left tapered surface 340 and the right tapered surface 342 may be angled the same angle such that angle β is equal to angle λ. However, in other embodiments, the left tapered surface 340 and the right tapered surface 342 are angled at different angles. For example, angle β may be greater than angle λ, such that the left tapered surface 340 has a steeper taper than the right tapered surface 342. In other cases, angle λ may be greater than angle β, such that the right tapered surface 342 has a steeper taper than the left tapered surface 340.

The body 300 may have any other suitable outer surfaces. For example, the body 300 may have a relatively flat front surface 344 and a relatively flat back surface 346. These surfaces may be completely flat or may be curved. The front surface 344 and back surface 346 may be generally oriented along the longitudinal axis 324 or may be angled with respect to the longitudinal axis 324. The flat surfaces 344, 346 may further reduce the outer profile of the body 300 to further reduce the chances of fit issues with the body 300 near bone and adjacent tissues.

Additionally, the body 300 may have a left side surface 348 and a right side surface 350. The left side surface 348 and right side surface 350 may curve around the exterior of the left or right arm 310, respectively, and at least a portion of the base 312. In some cases, the side surface 348, 350 may be flat. For example, the left side surface 348 may contact the left tapered surface 340 and the front surface 344 and the back surface 346. Similarly, the right side surface 350 may contact the right tapered surface 342, the front surface 344, and the back surface 346. The left side surface 348 and the right side surface 350 may be generally oriented along the longitudinal axis 324 or may be angled with respect to the longitudinal axis 324.

Although the base 312 is described as angling towards the right side of the body 300, it should be understood that the base 312 can be angled in any suitable direction, including to the left, front, or back of the body 300. Additionally, even though particular surfaces are described, any suitable surfaces for forming a biased angle body 300 are contemplated.

Figure 5A:
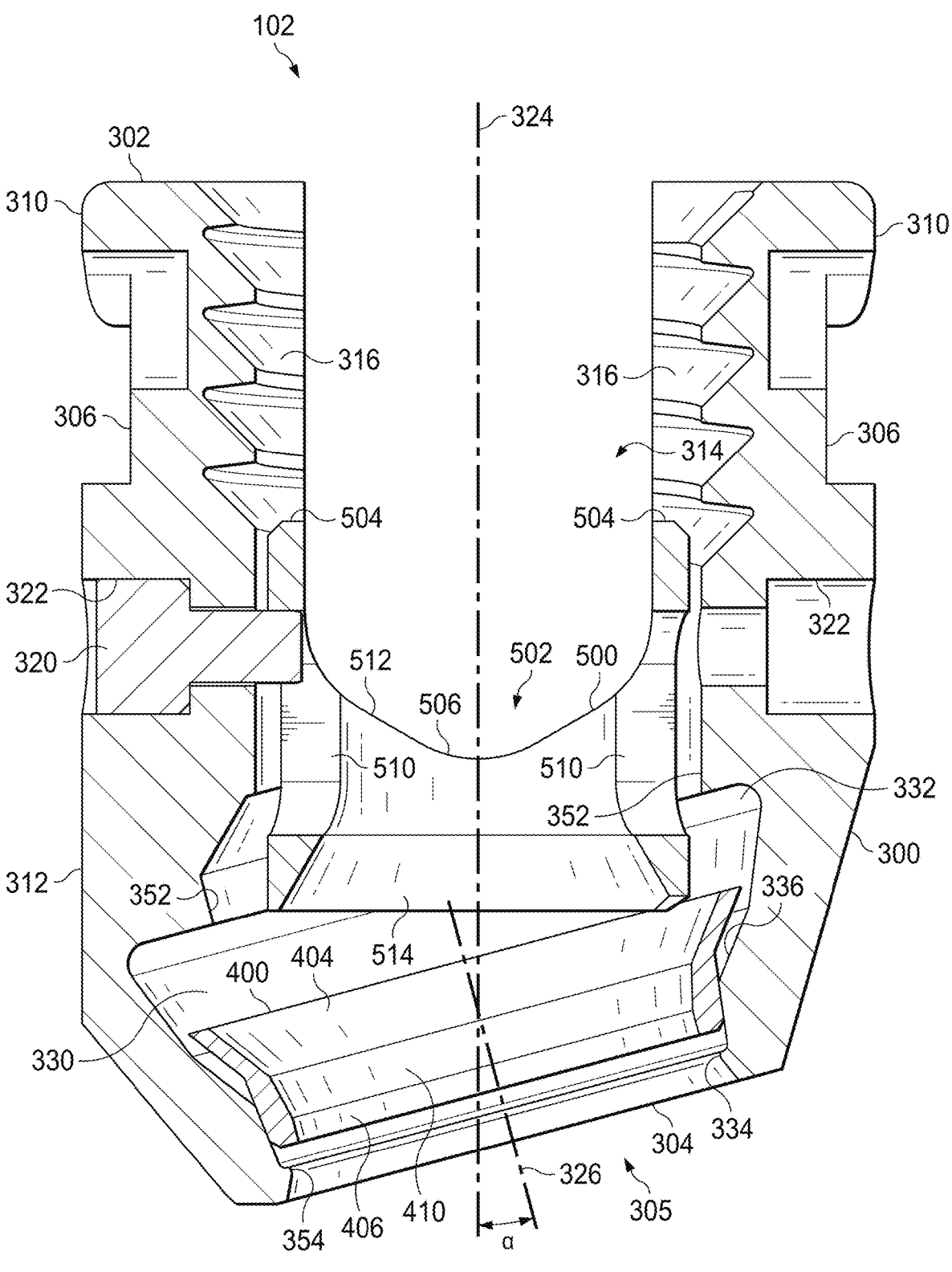
FIG. 5A is a cross-sectional view of a biased angle receiver for a pedicle screw assembly in accordance with some embodiments of the present disclosure.
Figure 5B:
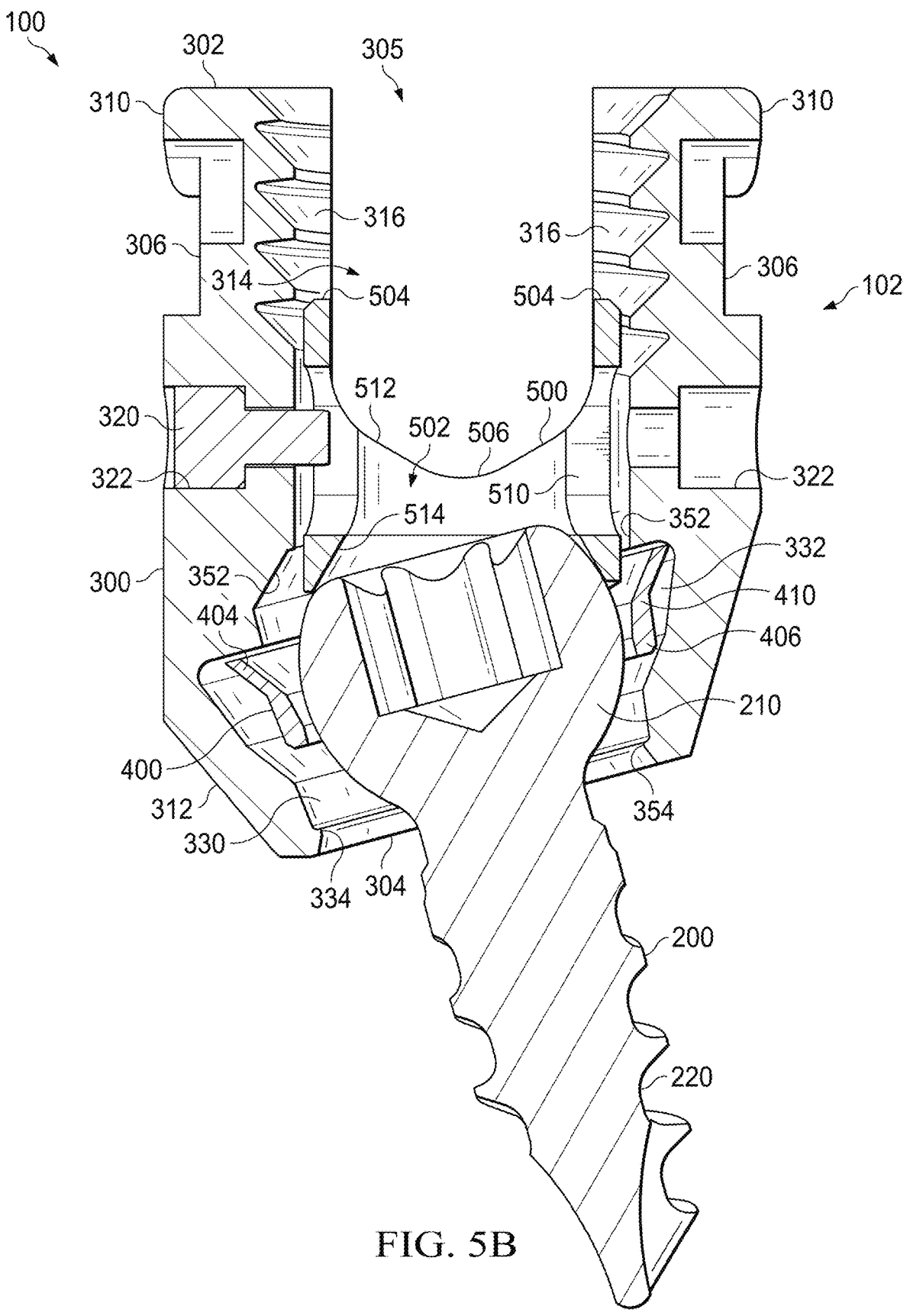
FIG. 5B is a cross-sectional view of a pedicle screw assembly, including the receiver shown in FIG. 5A and a screw, in accordance with some embodiments of the present disclosure.
Figure 5C:
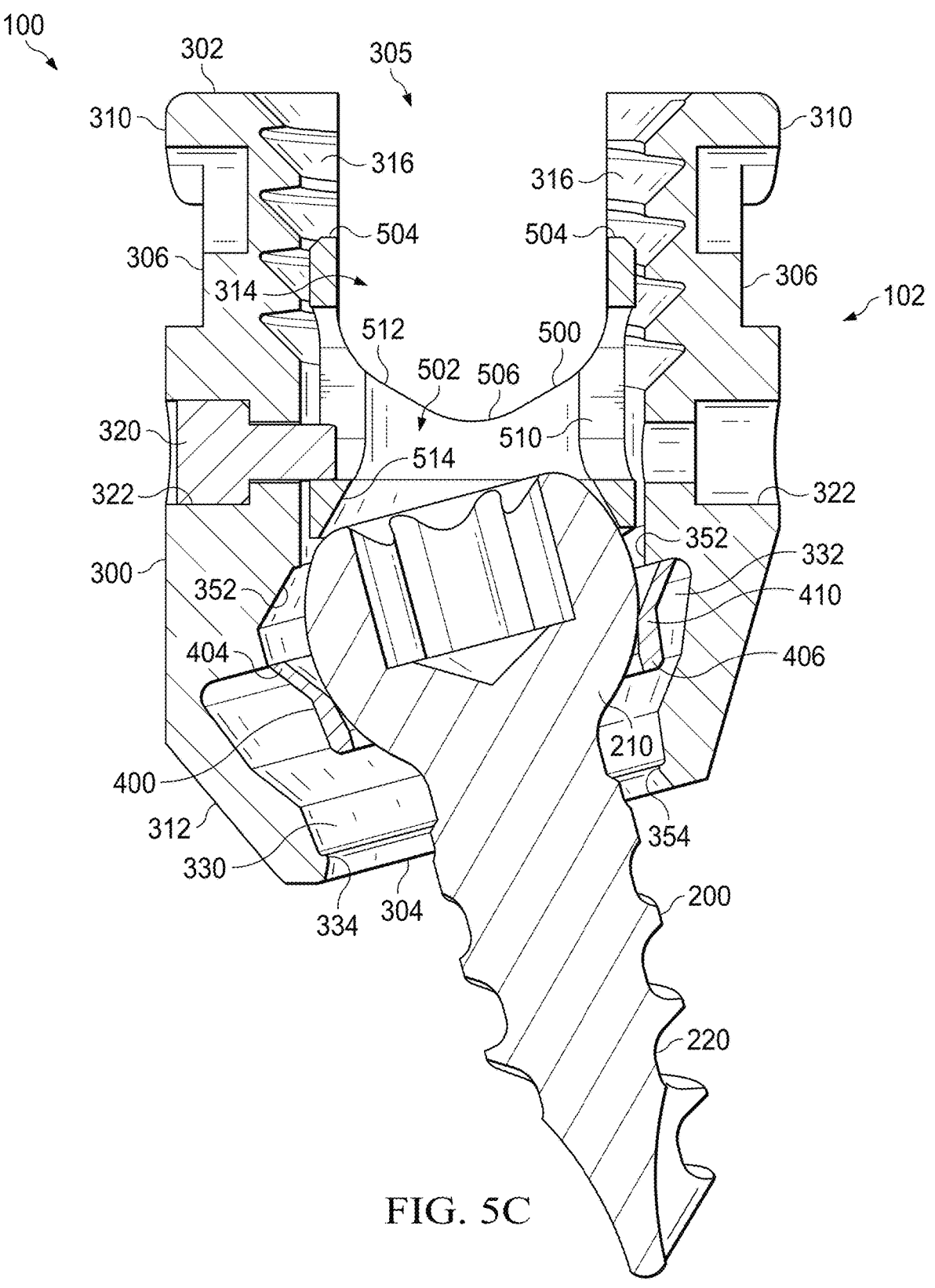
FIG. 5C is a cross-sectional view of a pedicle screw assembly, including the receiver shown in FIG. 5A and a screw, in accordance with some embodiments of the present disclosure.
Figure 5D:
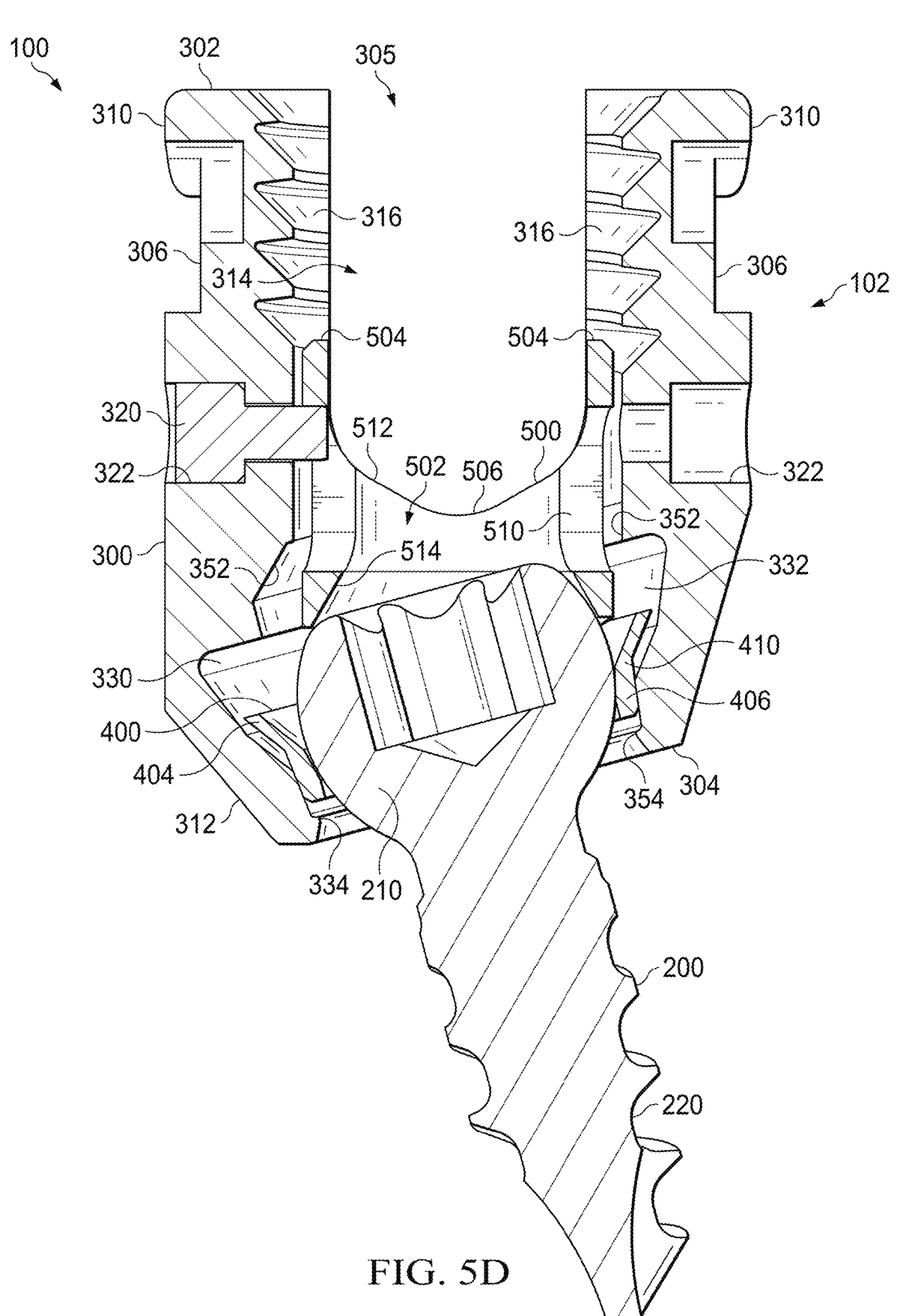
FIG. 5D is a cross-sectional view of a pedicle screw assembly, including the receiver shown in FIG. 5A and a screw, in accordance with some embodiments of the present disclosure.

FIGS. 5A-5D show a cross-section of the receiver 102 and how the receiver 102 may allow for bottom-loading of the screws 200 through the bottom 304 of the opening 305 of the body 300, according to some embodiments of the present disclosure. FIG. 5A shows a cross-sectional view of the receiver 102 through the arms 310 (according to the line shown in FIG. 2) without a screw 200 inserted. FIGS. 5B-5D show the same cross-sectional view as FIG. 5A, but of the assembly of the pedicle screw assembly 100 (the receiver 102 with a screw 200 inserted).

The opening 305 may extend from the top of the base 312 to the bottom 304 of the body 300. The opening 305 may open into the channel 314 of the body 300. The opening 305 may be aligned with the longitudinal axis 324 at the top and be angled along the bottom axis 326 at the bottom. In other embodiments, the opening 305 may smoothly transition between being aligned with the longitudinal axis 324 to being aligned with the bottom axis 326. However, in other embodiments, there may sharply transition between being aligned with the longitudinal axis 324 to being aligned with the bottom axis 326.

The body 300 may have a retainer ring chamber 330 configured to house the retainer ring 400 disposed around the opening 305. The chamber 330 may include an upper section 332 and a lower section 334. There may be a ledge 336 disposed between the upper section 332 and the lower section 334. In some embodiments, the upper section 332 may be wider than the lower section 334. The width of the upper section 332 may be equal to or larger than the width of the expanded retainer ring 400 to allow for the retainer 400 to expand. The width of the lower section 334 may be equal to or smaller than the width of the retainer ring 400 when it is contracted. If the retainer ring 400 comprises a lower portion 406 and a wider upper portion 404, the upper section 332 of the chamber 330 may be wide enough to allow the upper portion 404 of the retainer ring 400 to expand over the screw head 210, as described in more detail below. Moreover, the lower section 334 of the chamber 330 may be wide enough to fit the lower portion 406 of the retainer ring 400 when contracted but not wide enough to fit the upper portion 404. In other cases, the lower section 334 of the chamber 330 may be wide enough to fit both the upper portion 404 and the lower portion 406 of the retainer ring 400 when contracted.

In some embodiments, the chamber 330 may extend from the top to the bottom of the base 312. For example, the top of the upper section 332 of the chamber 330 may be proximate the top of the base 312 and the channel 314. The diameter or width of the channel 314 may be smaller than a width of the upper section 332 of the channel 314. There may be a rim, shoulder, or ridge 352 between the upper section 332 of the chamber 330 and the channel 314. The ridge 352 may be located around the top of the base 312. In some cases, the ridge 352 may have a different shape along the circumference of the opening 305. For example, the left side of the ridge 352 may be longer and may have a tapered section and the right side may be shorter and have a step.

In some cases, the bottom of the lower section 334 of the chamber 330 may be proximate the bottom of the base 312. There may be a lip 354 disposed between the lower section 334 of the chamber 330 and the bottom of the base 312. The lip 354 may have a width that is smaller than a width of the lower section 334 of the chamber 330. In some cases, the lip 354 may include a tapered, curved, or flat surface along the top and a skirt on the bottom that extends outward from a top of the lip 354 to the bottom 304 of the body 300. The lip 354 may provide additional protection so that the retainer ring 400 does not fall through the bottom of the body 300.

The upper section 332 of the chamber 330 may be angled such that it tapers inward from the top to the bottom. In other embodiments, the upper section 332 may not be tapered. Similarly, the lower section 334 may or may not be angled. The ledge 336 between the upper section 332 and the lower section 334 may be flat or may be angled such that it tapers inward from the upper section 332 to the lower section 334. The upper 332 and/or lower section 334 may be at least partially curved and may be conical in shape.

The chamber 330 may be generally aligned with the bottom axis 326. In other cases, the chamber 330 may be aligned with the longitudinal axis 324. In yet other cases, part of the chamber 330 may be aligned with the longitudinal axis 324 (ex. the upper section 332) and part may be aligned with the bottom axis 326 (ex. lower section 334) or the chamber 330 may not be aligned with either axis 324, 326.

In some cases, the chamber 330 may have a different shape that that described above or shown in the illustrated embodiments. In some embodiments, the chamber 330 does not have distinct upper 332 and lower 334 sections, but tapers from the top to the bottom. In some embodiments, chamber 330 may not allow the retainer ring 400 to move up and down and may only allow the retainer ring 400 to expand outward. In other embodiments, the body 300 may not have a chamber 330 and instead may be attached to the wall of the opening 305 through another suitable method.

The pressure cap 500 may be disposed in the body 300 such that it is disposed in both the channel 314 and the opening 305. In some cases, the pressure cap 500 may extend into the retainer ring chamber 330. The pressure cap 500 may move upwards to be mostly or entirely within the channel 314 or may move downwards to be mostly or entirely within the opening 305. The pressure cap 500 may be aligned with the longitudinal axis 324. In other cases, the pressure cap 500 may be angled with respect to the longitudinal axis 324 and, in some cases, may be aligned with the bottom axis 326.

In some embodiments, the pedicle screw assembly 100 may be configured for assembly before or during a surgical procedure. For example, the physician may select the screw 200 based on the patient's anatomy and indications. In some embodiments, the screw 200 may be selected after the surgery has begun and after the surgeon has created an access through the patient's tissue to the bone. In other instances, the physician and/or surgeon may select the screw 200 before the surgery based on medical images of the patient's anatomy (e.g., x-ray, computed tomography, magnetic resonance imaging).

In some cases, a physician may load the screw 200 into the receiver 102 to form a pedicle screw assembly 100 prior to inserting and driving the screws 200 into the patient's bone. The bottom-loading style of the assembly may be referred to as a modular assembly. The bottom-loaded modular assembly may be advantageous. For example, the modular assembly style of the receivers 102 may allow for the physician to choose a type and/or size of screw and assemble the receiver 102 and screw 200 during a spinal fixation procedure, based on the patient's anatomy and indications. The modular style may also allow for quick and efficient assembly with little or no disassembly of the receiver 102.

The upper surface of the screw head 210 may include a spherical, aspherical, or otherwise curved shape configured to engage the bottom surface of the pressure cap 500. In other embodiments, the screw head 210 may include a conic section shape. Accordingly, the screw head 210 may be curved about at least one axis to allow the screw head 210 to continuously rotate relative to the pressure cap 500. In other embodiments, the screw head 210 may include a polygonal shape having a plurality of flat surfaces arranged around an axis of the screw 200. For example, the screw head 210 may include, on the upper surface, 10, 20, 25, 30, or any other suitable number of flat surfaces arranged around the axis of the screw 200. The number of flat surfaces on the upper surface of the screw head 210 may correspond to the number of possible orientations of the receiver 102 about the longitudinal axis of the screw 200. In some embodiments, the pressure cap 500 may include corresponding polygonal surfaces on the bottom side or surface of the pressure cap 500.

The screw 200 includes a distal threaded shaft 220 comprising screw threads configured to drive into and engage the patient's bone. In the illustrated embodiment, the threads are right-handed threads. In other embodiments, the threads may be left-handed. The threads may have any suitable pitch, depth, and/or other geometric characteristics based on the target bone or tissue and application for the assembly. The screw 200 may be machined, laser sintered, 3D printed, or otherwise manufactured by any suitable manufacturing process. It will be understood that the threaded portion of the shaft of the screw 200 may extend a greater or lesser portion of the shaft than what is shown in FIGS. 5B-5D.

The receiver 102 may be assembled by placing the retainer ring 400 in the chamber 330. The retainer ring 400 may sit in the chamber 330 or may be affixed to the chamber 330 using, for example, an adhesive. The retainer ring 400 may be inserted into the opening 305 through either the top 302 or bottom 304 of the body 300. Moreover, the pressure cap 500 may be inserted into the opening 305 such that the slots 510 align with the pin holes 322. The pin 320 may then be inserted through one of the pin holes 322 and the slot 510. The pin 320 may be affixed to the pin hole 322 by any suitable means including by, for example, a mechanical lock or an adhesive. In some cases, the retainer ring 400 may be placed in the body 300 first, followed by the pressure cap 500 and the pin 320. In other cases, the pressure cap 500 may be inserted into the opening 305 first followed by the pin 320 and the retainer ring 400.

The pedicle screw assembly 100 may be assembled by inserting the screw 200 through the bottom 304 of the receiver 102 until it is locked therein. FIGS. 5A-5D show the pedicle screw assembly 100 as it is being assembled. Before the screw head 210 is inserted (as shown in FIG. 5A), the retainer ring 400 may be initially disposed at the region of the ledge or shoulder 336 between the upper 332 and lower 334 sections before the screw 200 is inserted. Thus, the retainer ring 400 may not be disposed only in the upper section 332 or only in the lower section 334, but may extend between both sections 332, 334. In some cases, the retainer ring 400 may only be disposed in the upper section 332.

Moreover, before the screw head 210 is inserted, the pressure cap 500 may be mostly disposed within the base 312 of the body 300 such that the pin 320 is located at the top or in the top section of the slot 510. In other cases, the pin 320 may be located in the middle, bottom section, or bottom of the slot 510.

FIG. 5B shows a cross section of the pedicle screw assembly 100 as the screw 200 is being pushed upwards through the bottom 304 of the receiver 102. As the screw head 210 is pushed upwards, the retainer ring 400 is pushed upward from being disposed between the upper 332 and lower 334 sections of the chamber 330 into the wider upper section 332 of the chamber 330. As the screw head 210 pushes upward on the retainer ring 400 it may also push outward on the retainer ring 400 such that the retainer ring 400 expands around the screw head 210 in the upper section 332. Moreover, the top of the screw head 210 contacts the bottom of the pressure cap 500 as it is pushed upwards, moving the pressure cap 500 upwards through the opening 305 and the channel 314. As the pressure cap 500 moves upwards, the slot 510 moves along the pin 320. The pin 320 also prevents the pressure cap 500 from rotating within the opening 305 and channel 314, thus maintaining the orientation of the pressure cap 500 and only allowing it to move upwards and downwards. In some embodiments, the pressure cap 500 may be pivotable in the body 300 such that the pressure cap 500 can pivot as the screw head 210 pressed upward against it, allowing the bottom surface 514 to better contact the screw head 210.

FIG. 5C shows the pedicle screw assembly 100 when the screw head 210 is pushed up to the furthest point within the body 300 of the receiver 102. As described above, the upper section 332 of the chamber 330 may be wider than the lower section 334, giving the retainer ring 400 additional room to expand when the retainer ring 400 is pushed to the top of the chamber 330. This may allow the screw head 210 to press the retainer ring 400 upward and outward such that the screw head 210 passes through the expanded retainer ring 400. Once the retainer ring 400 has passed over the widest part of the screw head 210, the retainer ring 400 may contract, locking the screw head 210 into the receiver 102, as shown in FIG. 5C. In some embodiments, the retainer ring 400 may contract to a width slightly larger than the width of the lower section 334 of the chamber 330. In some cases, only the upper portion 404 of the retainer ring 400 is wider than the lower section 334 of the chamber 330, such that the lower portion 406 of the retainer ring 400 can fit into the lower section 334 of the chamber 330. In other cases, the width of both the upper portion 404 and the lower portion 406 of the retainer ring 400 may be wider than the width of the lower section 334 of the chamber 330 when contracted.

When the screw 200 is pressed to its maximum position within the receiver 102, the pressure cap 500 may also be disposed at a maximum position within the body 300 such that the pin 320 contacts the bottom of the slot 510 within the pressure cap 500. The pin 320 may prevent the screw 200 from moving further up into the body 300 by preventing the pressure cap 500 from moving further up within the body.

FIG. 5D shows the pedicle screw assembly 100 after assembly. After the screw 200 is pressed upward through the bottom 304 of the receiver 102, the upward pressure on the screw 200 can be removed, thus allowing the screw 200 to settle into an assembled configuration. The screw 200 may be move downward slightly within the receiver 102 such that the bottom of the screw head 210 rests within the base 312 of the body 300. The lower surface of the screw head 210 may rest on a complementary upper surface of the retainer ring 400.

In some embodiments, as the retainer ring 400 contracts, the retainer ring 400 may move downward in the chamber 330. The screw head 210 may also press downward on the retainer ring 400 as it moves downward within the receiver 102. When the screw head 210 is seated within the receiver 102, the retainer ring 400 may be extend across the ledge 336 such that it is disposed between the upper 332 and lower 334 sections of the chamber 330. Thus, the lower portion 406 of the retainer ring 400 may be disposed completely or partially within the lower section 334 of the chamber 330 and the upper portion 404 of the retainer 400 may be completely or partially disposed within the upper section 332 of the chamber 330. However, in other cases, the retainer ring 400 may rest on the ledge 336 of the chamber 330 such that both portions 404, 406 of the retainer ring 400 are disposed within the upper section 332 of the chamber 330.

As the screw 200 moves downward, the pressure cap 500 may move downward as well such that the bottom surface 514 of the pressure cap 500 maintains contact with the top of the screw head 210. The slot 510 of the pressure cap 500 may slide downward such that the pin 320 is located at the middle, in the top section, or at the top of the slot 510.

In other embodiments, the screw 200 may not move downward when the upward force is removed. Accordingly, the pressure cap 500 may not move downward when the upward force is removed from the screw 200. In some embodiments, the retainer ring 400 may not move downward when the upward force is removed from the screw 200. Instead, the retainer ring 400 may remain in the same location and may contract. In other embodiments, the retainer ring 400 may not contract and may remain expanded. In yet other embodiments, the retainer ring 400 may move downward in the chamber 330 even if the screw 200 does not move downward.

Although the above description describes the components as moving upward or downward, it should be understood that upward (or upwards) may mean generally upward and downward (or downwards) may mean generally downward. The components may move upwards or downwards along the longitudinal axis 324 of the body 300 and other components may move upwards or downwards along the bottom axis 326. For example, the retainer ring 400 may be aligned with the bottom axis 326 and move upwards and downwards along the bottom axis 326. The pressure cap 500 may be aligned with the longitudinal axis 324 and may move upwards and downwards along the longitudinal axis 324. However, the components may also move at any angle relative to the axes 324, 326. For example, the screw 200 may be inserted along the bottom axis 326, the longitudinal axis 324, or any other suitable angle relative to these axes 324, 326.

When the screw 200 is seated within the receiver 102, the screw 200 may pivot, move, swivel, or rotate within the receiver 102 through a variety of angles relative to the longitudinal 324 and bottom 326 axes. The pressure cap 500 and/or the retainer ring 400 may apply a frictional force to the screw head 210 to hold the screw in a desired orientation relative to the receiver 102.

The materials of the receiver 102 may be biocompatible and may have other structural characteristics suitable for use in spinal fixation. For example, the body 300, pressure cap 500, pin 320, retainer ring 400, and/or the screw 200 may include a biocompatible metal, such as stainless steel, titanium, and/or alloys thereof. In other embodiments, one or more components of the receiver 102 may include a polymer material, such as DELRIN, polyetheretherketone (PEEK), polytetrafluorocthylene (PTFE), polysulfone (PS), polycarbonate, and/or any other suitable polymeric material. One or more components of the receiver 102 may be manufactured by milling, machining, casting, molding, laser sintering, 3D printing, and/or any other suitable process. The components of the receiver 102 may be formed of the same materials or of different materials, or any combination thereof.

Figure 6A:
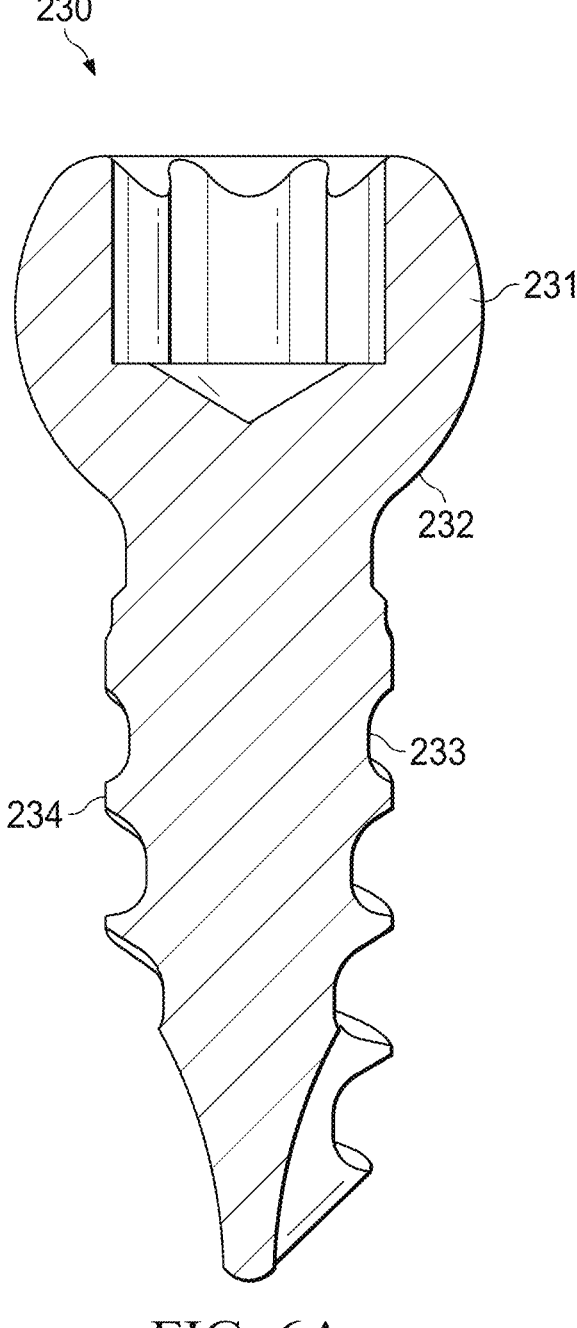
FIG. 6A is a front view of a screw for use in a biased angle pedicle screw assembly in accordance with some embodiments of the present disclosure.
Figure 6B:
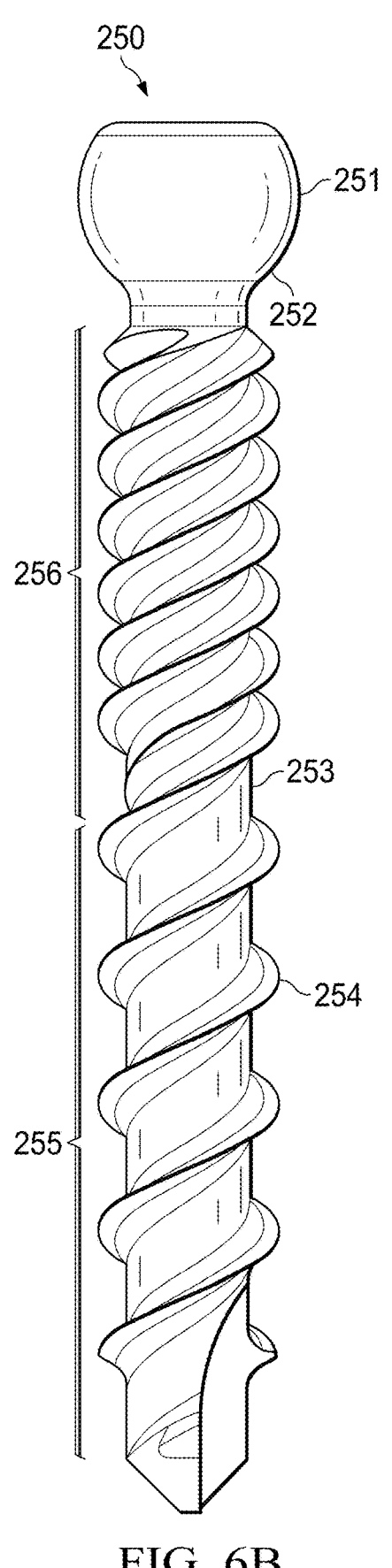
FIG. 6B is a front view of a screw for use in a biased angle pedicle screw assembly in accordance with some embodiments of the present disclosure.
Figure 6C:
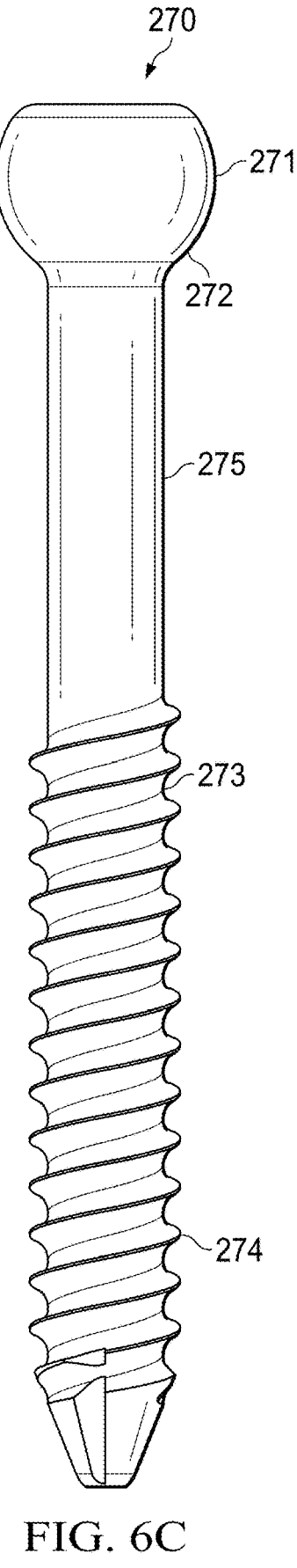
FIG. 6C is a front view of a screw for use in a biased angle pedicle screw assembly in accordance with some embodiments of the present disclosure.

FIGS. 6A-6C show various embodiments of a screw 200 for use in the pedicle screw assembly 100. FIG. 6A illustrates a dual lead pitch screw 230 as shown in FIGS. 1, 5B-5D. In the illustrated embodiment, the dual lead pitch screw 230 comprises a head 231 having a spherical-shaped bottom 232 and a shaft 233. The shaft 233 comprises threading 234 that extends along the length of the shaft 233. The threading 234 of the dual lead pitch screw comprises two starts. The dual lead pitch screw 230 may be advantageous for use in cortical bone. However, in other embodiments, the screw 250 may not be dual lead and instead may have one start or more than two starts. Moreover, the screw 250 may have any suitable pitch or lead.

FIG. 6B illustrates a part dual lead, part single lead screw 250. This embodiment comprises a head 251 having a spherical-shaped bottom 252 and a shaft 253. The shaft 253 comprises a threading 254 that extends completely or partially down the length of the shaft 253. Unlike the embodiment illustrated in FIG. 6A, the threading 254 in the embodiment illustrated in FIG. 6B comprises a first portion 255 that has one start and a second portion 256 that has two starts. The first portion 255 and the second portion 256 may be any suitable length. This embodiment may be advantageous for use in bone that comprises a cortical layer and a cancellous layer. In other embodiments, the threading may comprise any suitable number of portions with any suitable number of starts. Moreover, the screw 250 may have any suitable pitch or lead.

FIG. 6C illustrates a smooth shank screw 270. This embodiment comprises a head 271 having a spherical-shaped bottom 272 and a shaft 273. In this embodiment, the shaft 273 comprises threading 274. The threading 274 in screw 270 illustrated in FIG. 6C has threading 274 that extends partially along the length of the shaft 273. Thus, in an embodiment illustrated FIG. 6C, the screw 270 comprises a smooth portion 275 between the threading 274 and the head 271. The length of the smooth portion 275 may be any suitable length. Moreover, the screw 270 may comprise any suitable number of starts and may comprise multiple portions with different numbers of starts.

Any of the screws described herein may be any suitable length. For example, the screws may be 20 mm, 25 mm, 30 mm, 35 mm, 40 mm, 45 mm, 50 mm, 55 mm, 60 mm, or any other length.

The receiver 102 of the pedicle screw assembly 100 may be compatible with any of the screws 230, 250, 270 shown in FIGS. 6A, 6B, 6C, respectively, or any other suitable screw according to the embodiments contemplated by the present disclosure. Thus, the same receiver 102 may be used for any suitable screw 200. This allows the physician to have one type of receiver 102 but choose the desired screw 200 during the procedure. In other aspects, the receiver 102 may be specifically sized, shaped, or otherwise configured for use for one type of screw 200 but not for a different type of screw. Moreover, in some embodiments, any of the screws described herein may be used for both the biased angle receivers 102 described herein or any other modular receivers 102. Thus, this allows the physician to choose a desired type of receiver 102 and a desired screw 200 during the procedure.

Figure 7:
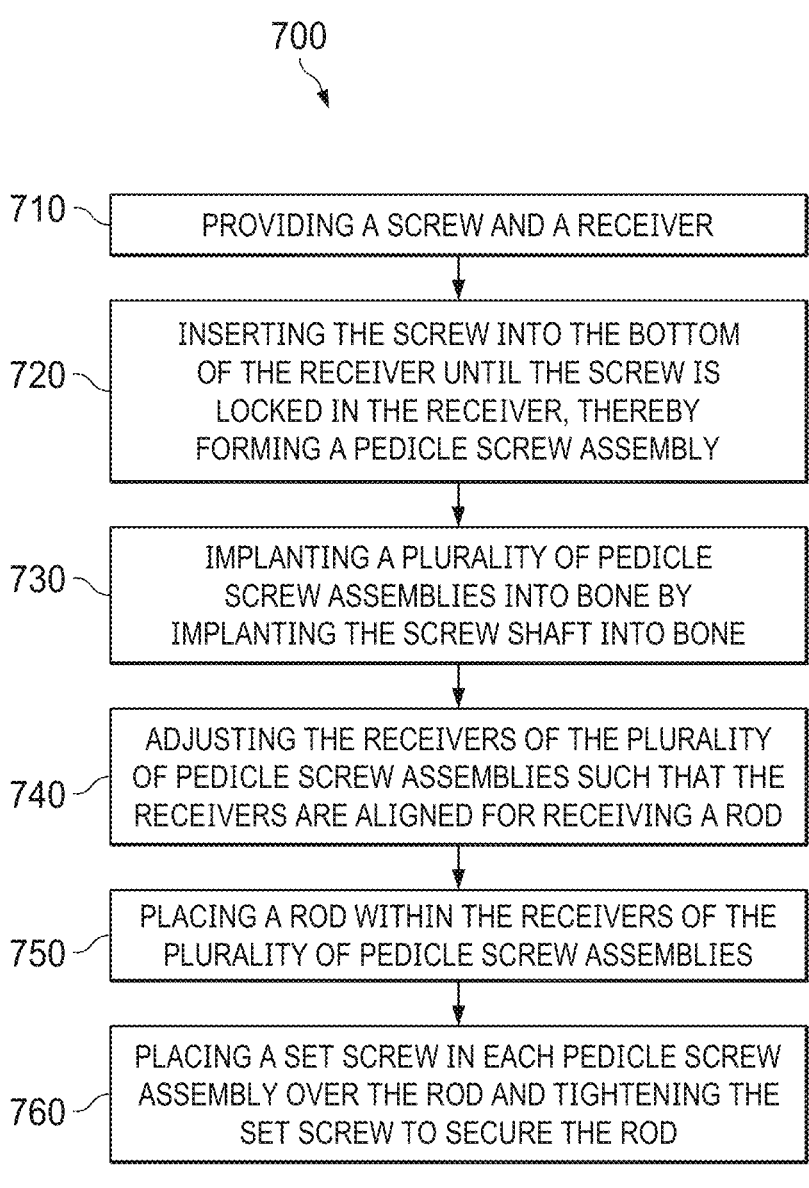
FIG. 7 is a flow chart illustrating a method of implanting a biased angle pedicle screw assembly in accordance with some embodiments of the present disclosure.

FIG. 7 shows a method 700 of assembling for treating a spinal condition using the pedicle screw assembly 100. Step 710 of the method 700 includes providing a screw 200 and a receiver 102. The receiver 102 may be any receiver 102 described herein, including any of the receivers 102 or parts of receivers 102 shown in FIGS. 1-5D. Thus, the receiver 102 may be, for example, a biased angle receiver 102. The screw 200 may be any screw 200 described herein, including the screws 200 shown in FIG. 1, 5B-5D, or 6A-6C. The surgeon or technician may select a receiver 102 and screw 200 from a plurality of receivers 102 and screws 200 based on the patient's anatomy and/or indications.

Step 720 of the method includes inserting the screw 200 into the bottom 304 of the receiver 102 until the screw 200 is locked in the receiver 102, thereby forming a pedicle screw assembly 100. As the screw 200 moves upward through the receiver 102, the retainer ring 400 may expand over the head 210 of the screw and the pressure cap 500 may be pressed upward as described in reference to FIGS. 5B-5C. When the upward force is removed from the screw 200, the screw 200 may move downward slightly to rest in the base 312 of the body 300. As the screw 200 moves downward, the retainer ring 400 may contract and move downward and the pressure cap 500 may move downward as described in reference to FIG. 5D. However, the screw 200 may be inserted into and be locked in the receiver 102 in any suitable way.

Step 730 of the method 700 includes implanting a plurality of pedicle screw assemblies 100 into bone by implanting the screw shaft 220 into the bone. In some embodiments, the bone may be a vertebrae 110. As described herein, an instrument may releasably engage the engagement feature 306 of the receiver 102. The instrument may then be used to position the pedicle screw assembly 100 at the desired position. The same instrument or a different instrument may drive the screw 200 into the bone. For example, a screwdriver may pass through the opening 502 of the pressure cap 500 to access the screw head 210. The screwdriver may then be used to screw the screw shaft 220 into the bone. However, the screw 200 may be driven into the bone using any suitable method.

Step 740 of the method 700 includes adjusting the receivers 102 of the plurality of pedicle screws 100 such that the receivers 102 are aligned for receiving a rod 120. An instrument may engage with the engagement feature 306 of the receiver 102 to move the receiver 102 independent of the screw 200. The receiver 102 may be moved into any suitable position for receiving a rod. The pressure cap 500 and/or the retainer ring 400 may apply a frictional force to the screw head 210 to retain the position and orientation of the receiver 102 relative to the screw head 210.

Step 750 of the method 700 includes placing a rod 120 within the receivers 102 of the plurality of pedicle screw assemblies 100. Once the receivers 102 are aligned, a rod 120 may be placed such that it fits within the U-shaped channel 314 formed by the arms 310 of the receiver 102. The rod 120 may be bent or curved into the desired shape before or while placing the rod 120 into the receiver 102.

Step 760 of the method 700 includes placing a set screw 130 in each pedicle screw assembly 100 over the rod 120 and tightening the set screws 130 to secure the rod 120. Tightening the set screws 130 may also secure the position and orientation of the receivers 102 relative to the screws 200. The set screws 130 may be any suitable set screw 130 design, including the design described in reference to FIG. 1. The set screw 130 may have threads that engage the threads 316 of the arms 310 of the body 300. An instrument, like, for example, a screwdriver, may be used to tighten the set screw 130 until it contacts and presses against the rod 120. The set screws 130 may secure the rod 120 and/or the receivers such that they do not move. In some embodiments, the rod 120 may be tightened such that it stabilizes the vertebrae 110.

It will be understood that one or more embodiments described above may be modified in one or more ways without departing from the scope of the present disclosure. In some embodiments, a body may include fewer or more engagement features than the two engagement features shown above. In some embodiments, a receiver may not allow for modular assembly. For example, a receiver may not include the retainer ring illustrated above. In this regard, an implantable assembly may be configured such that a bottom surface of the screw head directly contacts a seating surface of the body. In some embodiments, the pressure cap may have a pin that fits into a slot of the body instead of the body having a pin that fits into the slot of the pressure cap as shown above.

Aspects, components, and features described above may be used in a variety of skeletal stabilization and/or fixation systems. For example, the biased angle receiver may be used in a non-modular construction or may be used in a variety of other contexts. Further, although embodiments of the present disclosure may be described as spinal implants or spinal fixation devices, it will be understood that the devices described above may be used for a variety of skeletal stabilization and/or fixation procedures.

Persons of ordinary skill in the art will appreciate that the implementations encompassed by the present disclosure are not limited to the particular exemplary implementations described above. In that regard, although illustrative implementations have been shown and described, a wide range of modification, change, combination, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

The invention claimed is:

1. An implantable receiver comprising:
a body configured to be coupled to a bone fastener and a rod for spinal stabilization, the body comprising a longitudinal axis, wherein the body further comprises:
a base defining an opening from a top end to a bottom end of the base, wherein a bottom axis of the bottom end of the base is obliquely angled with respect to the longitudinal axis;
a chamber defined within the base and in communication with the opening, wherein the chamber comprises an upper section, a lower section, and a tapered shoulder between the upper section and the lower section, wherein a chamber axis is obliquely angled with respect to the longitudinal axis; and
a channel oriented along the longitudinal axis and configured to receive a set screw for locking the rod to the body, wherein a diameter of the channel is smaller than a diameter of the upper section of the chamber; and
a retainer comprising a upper portion and a lower portion, wherein the retainer is disposed in the chamber between the upper section and the lower section, wherein the retainer is configured to expand in the upper section of the chamber to receive a bulbous head of the bone fastener up through a bottom opening of the retainer, wherein the upper portion of the retainer is wider than the lower section of the chamber, and wherein the upper portion of the retainer is wider than the lower portion of the retainer.

2. The receiver of claim 1, wherein the upper section of the chamber is wider than the lower section of the chamber.

3. The receiver of claim 1, wherein a top axis of the base is co-linear with the longitudinal axis.

4. The receiver of claim 1, wherein the chamber axis and the bottom axis are co-linear.

5. The receiver of claim 1, wherein a top of the upper portion of the retainer is proximate the top end of the base and a bottom of the lower portion of the retainer is proximate the bottom end of the base.

6. The receiver of claim 1, wherein the body comprises two opposing arms extending upwardly from the top end of the base and defining two lateral openings for receiving the rod through the channel.

7. The receiver of claim 1, wherein the base further comprises a lip disposed at a bottom of the lower section of the chamber and extending around at least a portion of a circumference of the lower section of the chamber.

8. The receiver of claim 1, wherein an outer surface of the body comprises a conical taper surrounding the chamber, the conical taper being oriented obliquely with respect to the longitudinal axis.

9. An implantable receiver comprising:
a body configured to be coupled to a bone fastener and a rod for spinal stabilization, the body comprising a longitudinal axis, wherein the body further comprises:

a base defining an opening from a top end to a bottom end of the base, wherein a bottom axis of the bottom end of the base is obliquely angled with respect to the longitudinal axis; and
a chamber defined within the base and in communication with the opening, wherein the chamber comprises an upper section, a lower section, and a tapered shoulder between the upper section and the lower section, wherein a chamber axis is obliquely angled with respect to the longitudinal axis;
a retainer comprising a upper portion and a lower portion, wherein the retainer is disposed in the chamber between the upper section and lower section, wherein the retainer is configured to expand in the upper section of the chamber to receive a bulbous head of the bone fastener up through a bottom opening of the retainer, and wherein the upper portion of the retainer is wider than the lower portion of the retainer; and
a pressure insert disposed in the opening at the top end of the base, the pressure insert comprising a downward-facing surface configured to contact a head of the bone fastener, wherein the pressure insert is configured to apply a downward force on the head of the bone fastener when the rod is secured in the receiver.

10. The receiver of claim 9, wherein the body further comprises a channel oriented along the longitudinal axis and configured to receive a set screw for locking the rod to the body, wherein a diameter of the channel is smaller than a diameter of the upper section of the chamber.

11. The receiver of claim 9, wherein the downward-facing surface of the pressure insert is concave.

12. The receiver of claim 11, wherein the pressure insert further comprises:
a pair of opposed sidewalls; and
an upward-facing surface curving between the pair of opposed sidewalls, wherein the upward-facing surface is saddle-shaped.

13. The receiver of claim 9, wherein the opening of the body is wider than the pressure insert such that the pressure insert is pivotable relative to an axis substantially perpendicular to the longitudinal axis.

14. The receiver of claim 9, further comprising a pin disposed in a pin hole in the body such that the pin extends into a slot in the pressure insert.

15. An implantable receiver comprising:
a body configured to be coupled to a bone fastener and a rod for spinal stabilization, the body comprising a longitudinal axis, wherein the body further comprises:
a base defining an opening from a top end to a bottom end of the base, wherein a bottom axis of the bottom end of the base is obliquely angled with respect to the longitudinal axis; and
a chamber defined within the base and in communication with the opening, wherein the chamber comprises an upper section, a lower section, and a tapered shoulder between the upper section and the lower section, wherein a chamber axis is obliquely angled with respect to the longitudinal axis;
a retainer comprising a first portion and a second portion, wherein the retainer is disposed in the chamber between the upper section and lower section, wherein the retainer is configured to expand in the upper section of the chamber to receive a bulbous head of the bone fastener up through a bottom opening of the retainer, and wherein the first portion of the retainer is wider than the second portion of the retainer;

a pressure insert disposed in the opening at the top end of the base, the pressure insert comprising a downward-facing surface configured to contact a head of the bone fastener, wherein the pressure insert is configured to apply a downward force on the head of the bone fastener when the rod is secured in the receiver; and a pin disposed in a pin hole in the body such that the pin extends into a slot in the pressure insert, wherein the pressure insert is pivotable about a longitudinal axis of the pin.

16. A modular bone fastener assembly, comprising:

a bone fastener, comprising:

a head comprising a spherical outer surface;

a shaft extending downwardly from the head; and a neck disposed between the head and the shaft; and a receiver comprising:

a body configured to be coupled to the bone fastener and a rod for spinal stabilization, the body comprising a longitudinal axis, wherein the body further comprises:

a base defining an opening from a top end to a bottom end of the base, wherein a bottom axis of the bottom end of the base is obliquely angled with respect to the longitudinal axis;

a chamber defined within the base and in communication with the opening, wherein the chamber comprises an upper section, a lower section, and a tapered shoulder between the upper section and the lower section, wherein a chamber axis is obliquely angled with respect to the longitudinal axis; and a channel oriented along the longitudinal axis, wherein a diameter of the channel is smaller than a diameter of the upper section of the chamber;

a retainer comprising a upper portion and a lower portion, wherein the retainer is expandable around the head and disposed in the channel between the upper section and the lower section, and wherein the upper portion of the retainer is wider than the lower portion of the retainer; and a pressure insert disposed in the opening at the top end of the base, the pressure insert comprising a downward-facing surface configured to contact a part of the spherical outer surface of the head; and a set screw receivable within the channel, wherein the set screw is configured to apply a downward force on the rod to secure the rod within the channel and a down-ward force on the pressure insert and the head of the bone fastener to secure the head of the bone fastener within the receiver.

17. The modular bone fastener assembly of claim 16, wherein the retainer is disposed around the neck of the bone fastener.

18. The modular bone fastener assembly of claim 16, wherein the set screw is configured to secure the head of the bone fastener between the pressure insert and the retainer.

19. The modular bone fastener assembly of claim 16, wherein the bone fastener is pivotable relative to the bottom axis.

20. An implantable receiver comprising:

a body configured to be coupled to a bone fastener and a rod for spinal stabilization, the body comprising a longitudinal axis, wherein the body further comprises:

a base defining an opening from a top end to a bottom end of the base, wherein a bottom axis of the bottom end of the base is obliquely angled with respect to the longitudinal axis;

a chamber defined within the base and in communication with the opening, wherein the chamber comprises an upper section, a lower section, and a tapered shoulder between the upper section and the lower section, wherein a chamber axis is obliquely angled with respect to the longitudinal axis; and a channel oriented along the longitudinal axis and configured to receive a set screw for locking the rod to the body, wherein a diameter of the channel is smaller than a diameter of the upper section of the chamber; and a retainer comprising a first portion and a second portion, wherein the retainer is disposed in the chamber between the upper section and the lower section, wherein the retainer is configured to expand in the upper section of the chamber to receive a bulbous head of the bone fastener up through a bottom opening of the retainer, wherein the first portion of the retainer is wider than the lower section of the chamber, and wherein the first portion of the retainer is wider than the second portion of the retainer, and wherein the first portion of the retainer is integral with the second portion of the retainer.

\* \* \* \* \*